(12) United States Patent
Chan

(10) Patent No.: US 7,108,700 B2
(45) Date of Patent: *Sep. 19, 2006

(54) SURGICAL REPAIR KIT AND ITS METHOD OF USE

(76) Inventor: Kwan-Ho Chan, 4702 S. Jackson, Joplin, MO (US) 64804

( * ) Notice: Subject to any disclaimer, the term of this patent is extended or adjusted under 35 U.S.C. 154(b) by 1068 days.

This patent is subject to a terminal disclaimer.

(21) Appl. No.: 09/811,953

(22) Filed: Mar. 19, 2001

(65) Prior Publication Data

US 2005/0165418 A1   Jul. 28, 2005

Related U.S. Application Data

(63) Continuation of application No. 09/111,237, filed on Jul. 7, 1998, now abandoned, which is a continuation of application No. 08/727,027, filed on Oct. 8, 1996, now Pat. No. 5,776,151, which is a continuation of application No. 08/234,840, filed on Apr. 28, 1994, now Pat. No. 5,562,683, which is a continuation-in-part of application No. 08/090,651, filed on Jul. 12, 1993, now Pat. No. 5,562,687.

(51) Int. Cl.
*A61B 17/04* (2006.01)

(52) U.S. Cl. .................. 606/148; 606/139; 289/17

(58) Field of Classification Search ............ 606/139, 606/144, 148, 222–224; 289/17
See application file for complete search history.

(56) References Cited

U.S. PATENT DOCUMENTS

| | | | |
|---|---|---|---|
| 916,708 A | 3/1909 | Holmes | |
| 1,180,975 A | 4/1916 | Chapman | |
| 1,270,639 A | 6/1918 | Malcom | |
| 2,286,578 A | 6/1942 | Sauter | |
| 2,406,838 A | 9/1946 | Kepler | |
| 2,455,833 A | 12/1948 | Trombetta et al. | |
| 2,595,758 A | 5/1952 | Brown et al. | |
| 3,472,231 A | 10/1969 | Niebel et al. | |
| 4,100,393 A | 7/1978 | Luther | |
| 4,177,813 A | 12/1979 | Miller et al. | |
| 4,414,908 A | 11/1983 | Eguchi et al. | |
| 4,545,374 A | 10/1985 | Jacobson | |
| 4,864,762 A | 9/1989 | Cox | |
| 4,923,461 A | 5/1990 | Caspari et al. | |
| 5,236,434 A | 8/1993 | Callicrate | |
| 5,263,936 A | 11/1993 | Yurino | |
| 5,334,199 A | 8/1994 | Yoon | |
| 5,342,369 A | 8/1994 | Harryman, II | |

(Continued)

FOREIGN PATENT DOCUMENTS

DE         453256         1/1929

(Continued)

*Primary Examiner*—Julian W. Woo
(74) *Attorney, Agent, or Firm*—Pandiscio & Pandiscio

(57) ABSTRACT

A suture passer comprises a longitudinally extending hollow cannula having a central passage slidingly receivable of a surgical suture; a manually graspable handle connected to the hollow cannula for manipulation thereof, the handle having an upper surface; first guide means, connected to the upper surface of the handle, proximate a distal end of the handle for releasably, guidingly, holding the surgical suture; second guide means, connected to the upper surface of the handle, proximate to the first guide means, for releasably, guidingly, holding the surgical suture. The suture passer can be provided in a kit, for use in the suturing of internal tissue, along with a cannula bender, various hollow surgical needles and surgical suture material. The suture passer finds particular use in the suturing of internal tissues which are at least partially accessible through a body cavity, e.g. arthroscopic surgery.

5 Claims, 44 Drawing Sheets

U.S. PATENT DOCUMENTS

| | | |
|---|---|---|
| 5,350,385 A | 9/1994 | Christy |
| 5,364,409 A | 11/1994 | Kuwabara et al. |
| 5,382,258 A | 1/1995 | Chow |
| 5,562,683 A * | 10/1996 | Chan .......................... 606/139 |
| 5,776,151 A * | 7/1998 | Chan .......................... 606/148 |

FOREIGN PATENT DOCUMENTS

| | | |
|---|---|---|
| SU | 0649416 | 2/1979 |
| SU | 1192881 | 11/1985 |

* cited by examiner

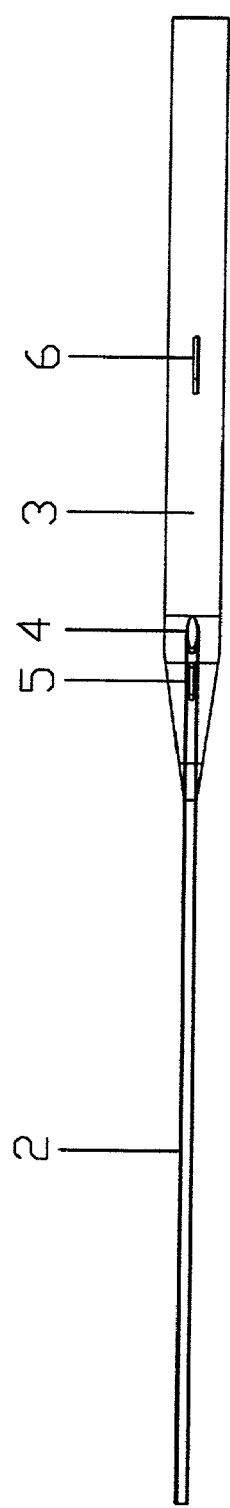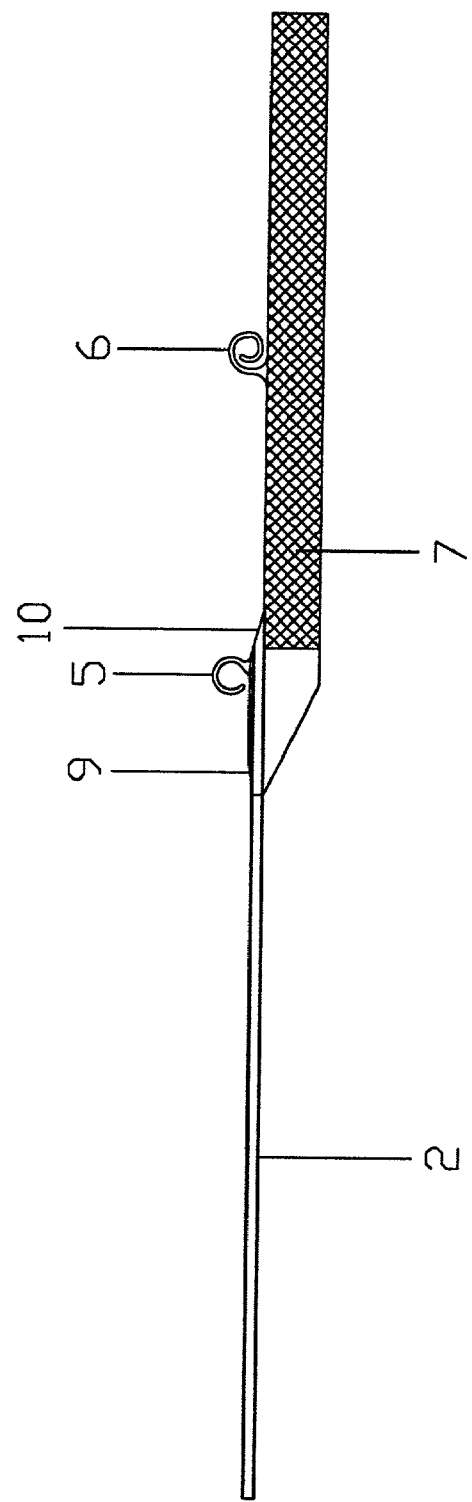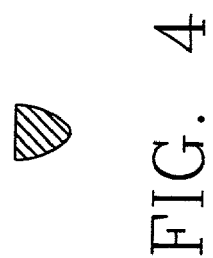

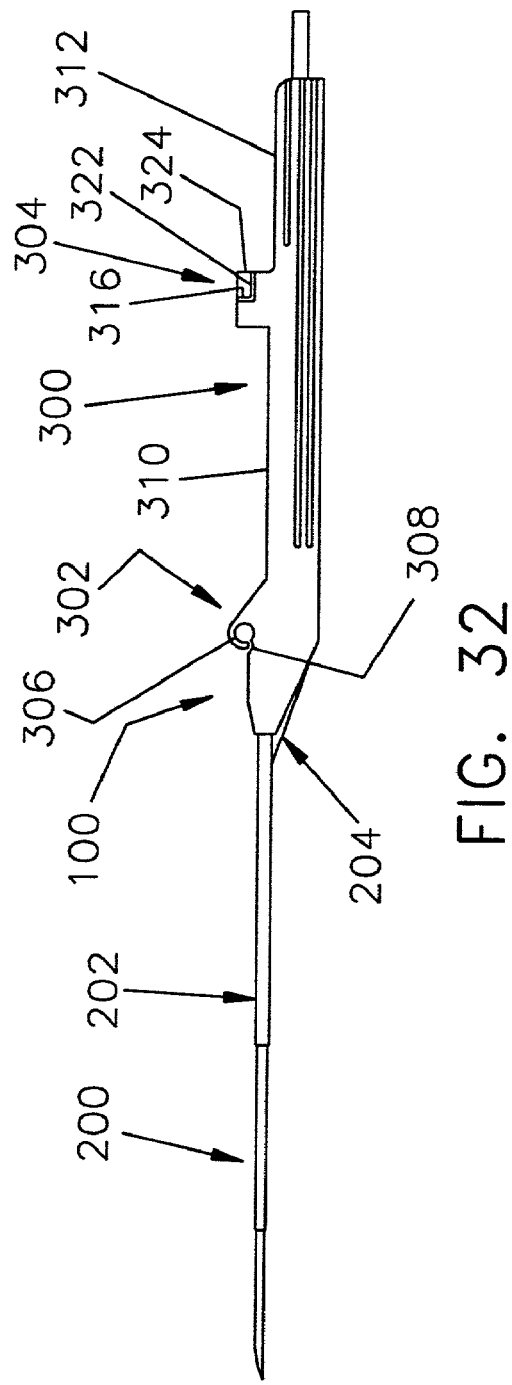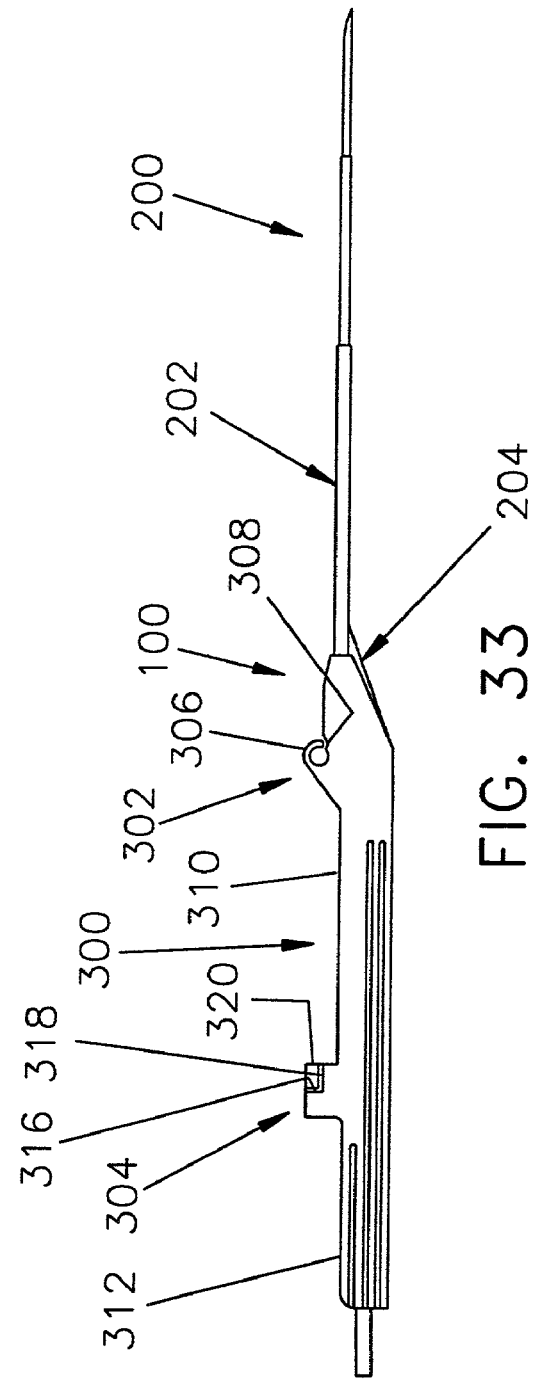

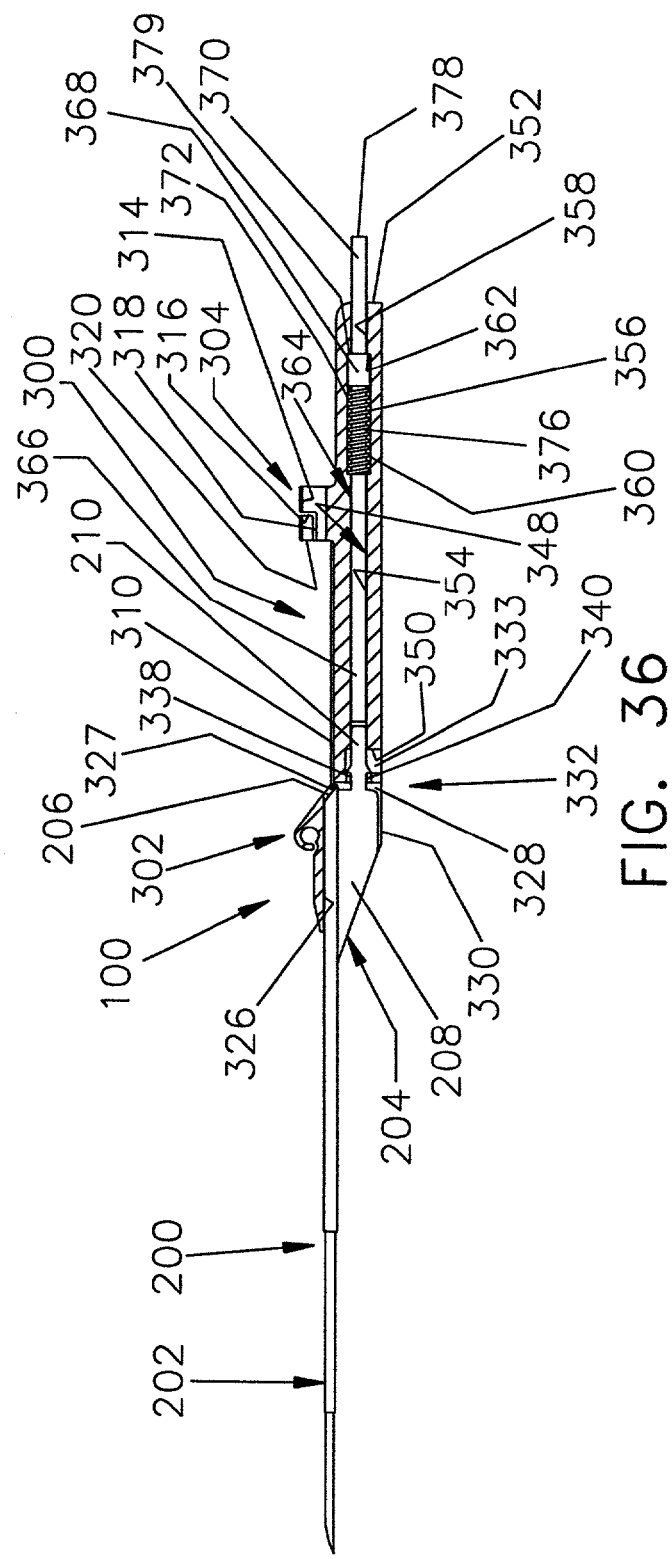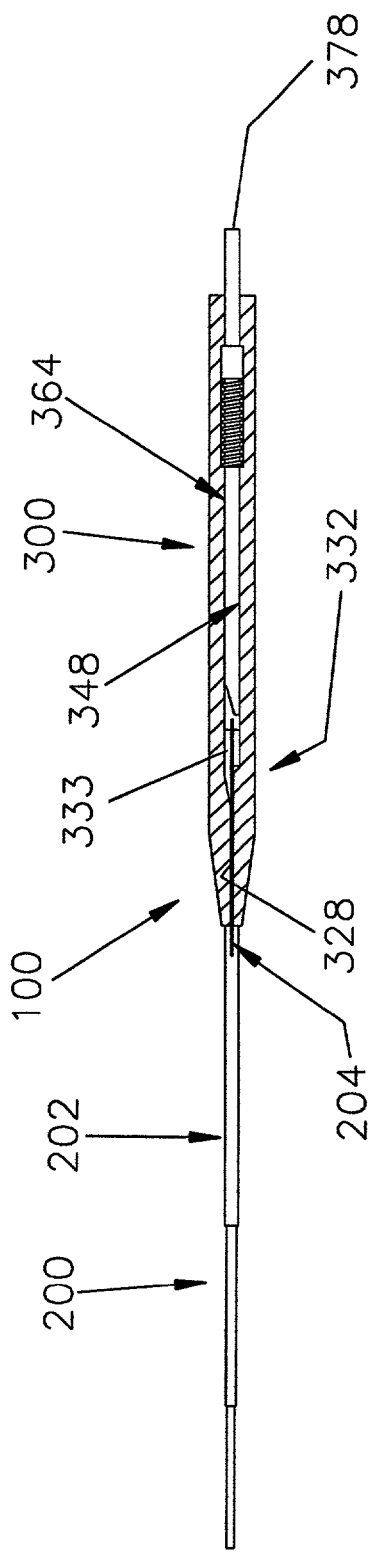

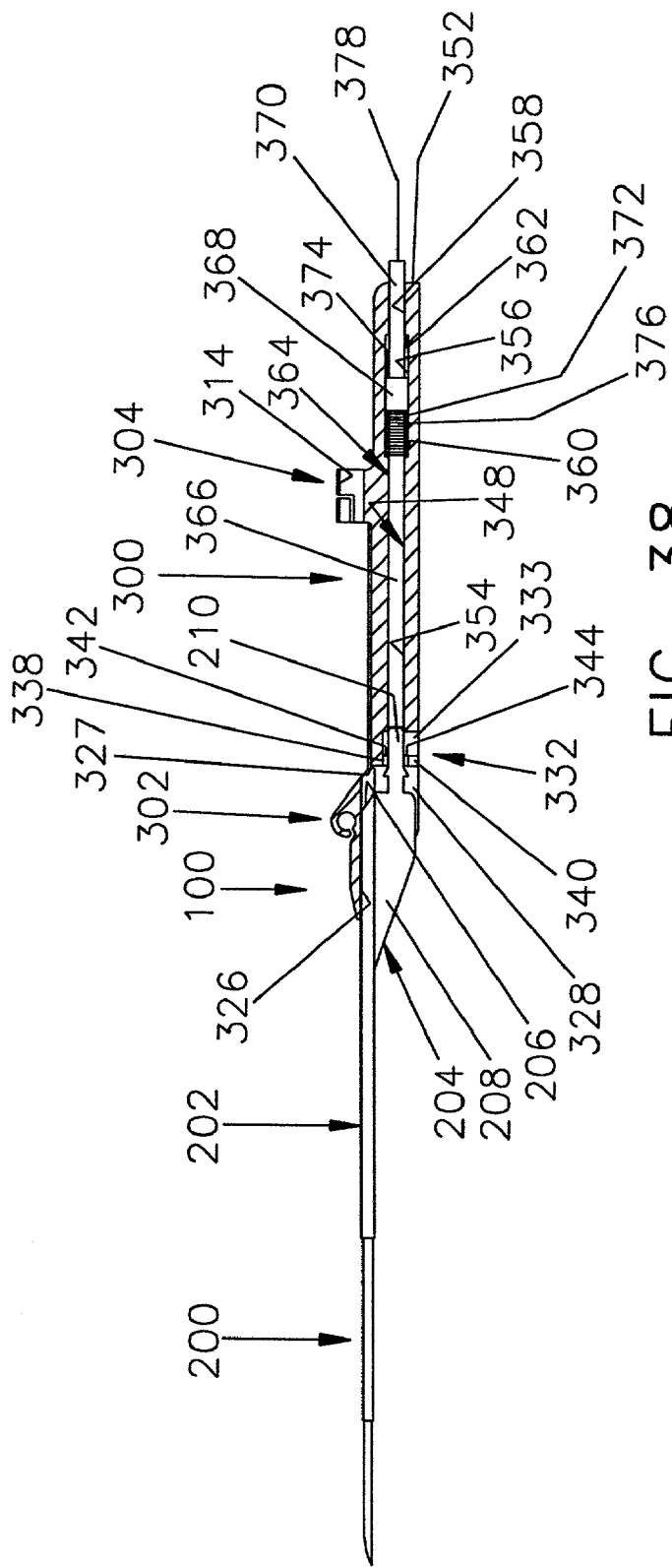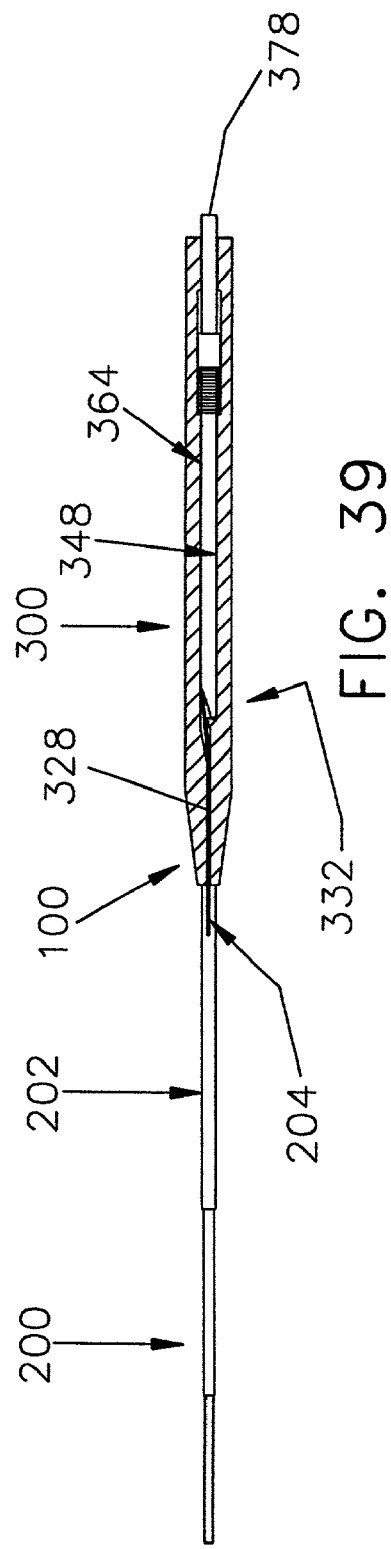
FIG. 38
FIG. 39

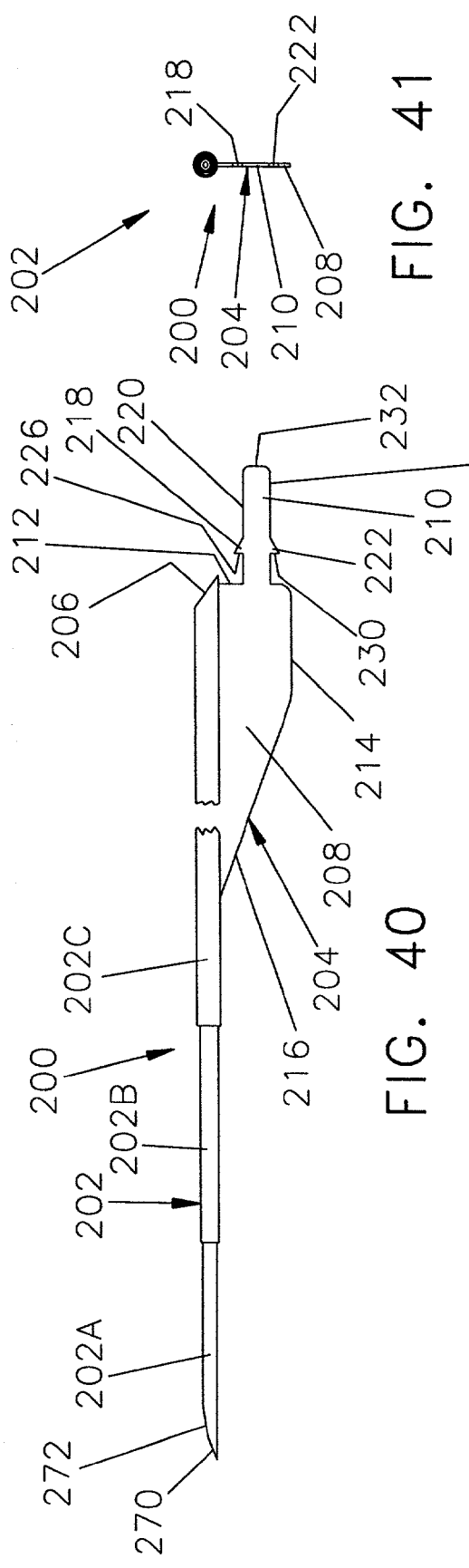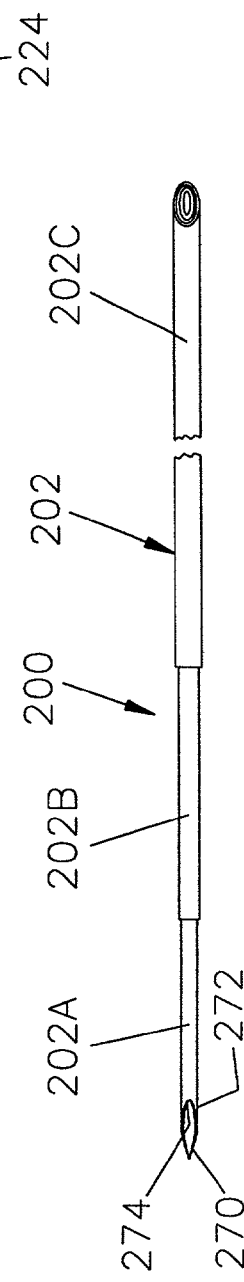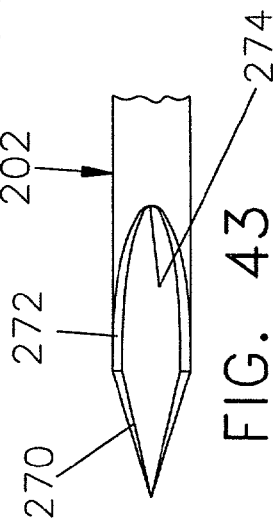
FIG. 40
FIG. 41
FIG. 42
FIG. 43

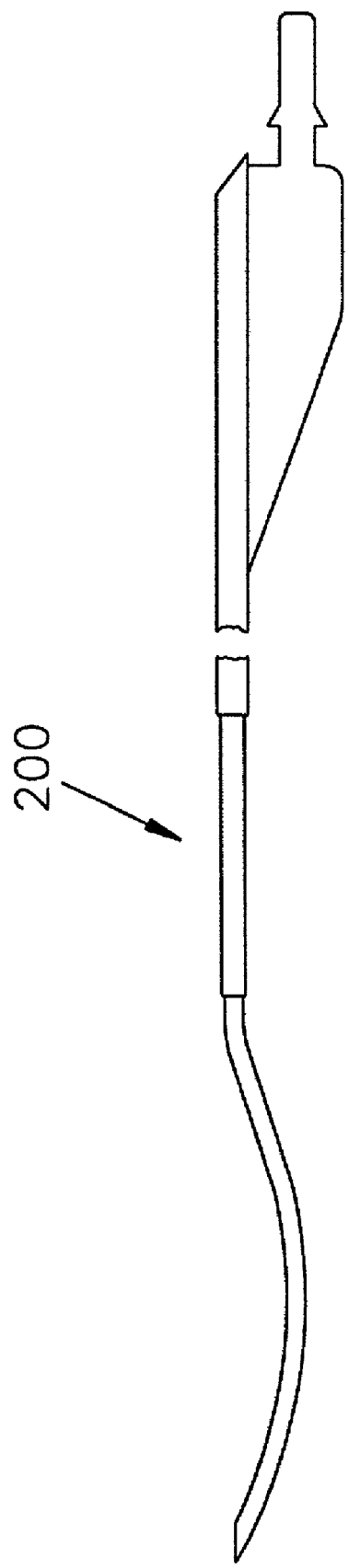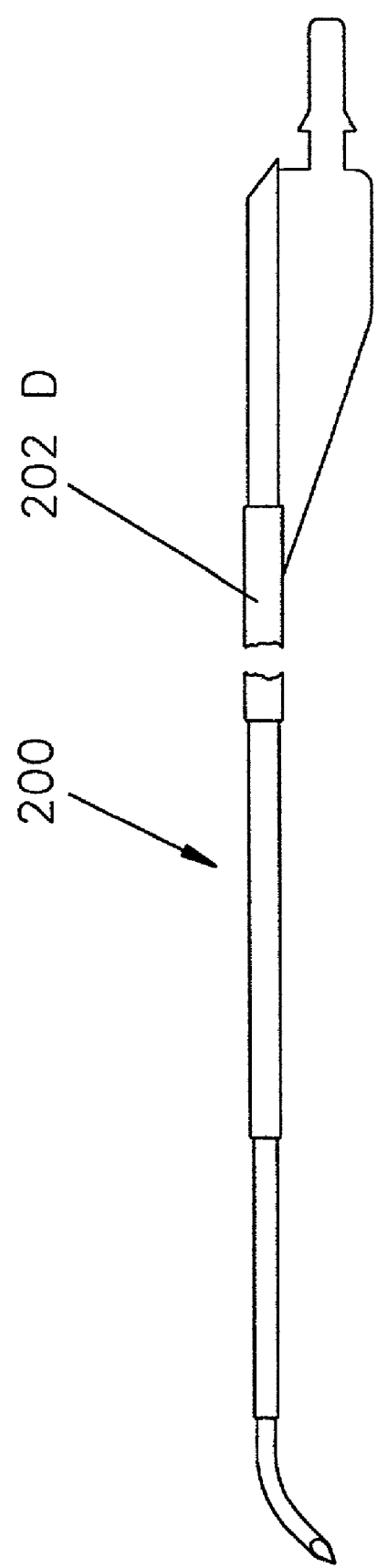

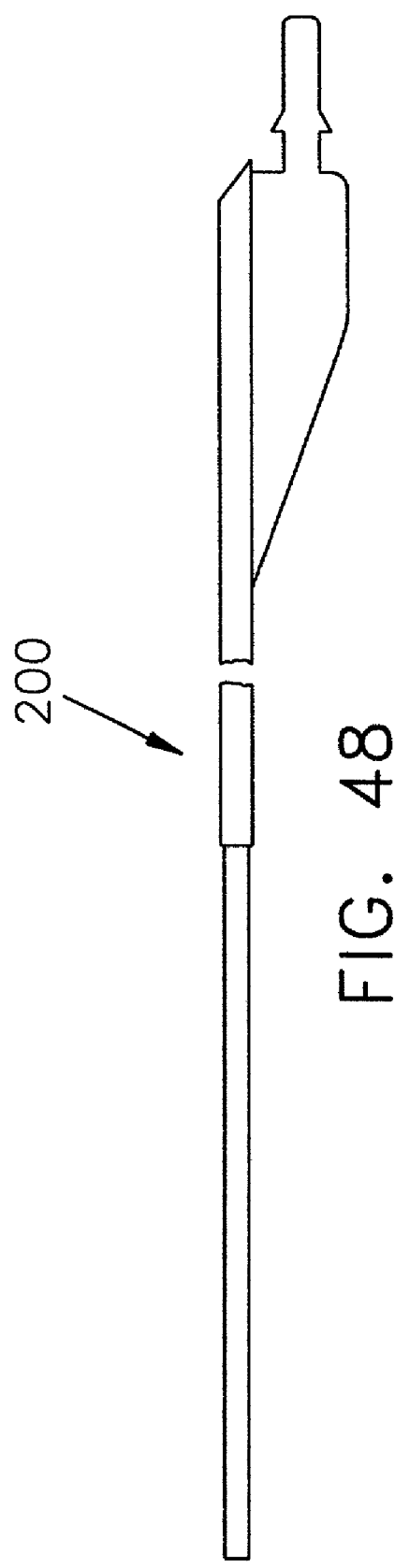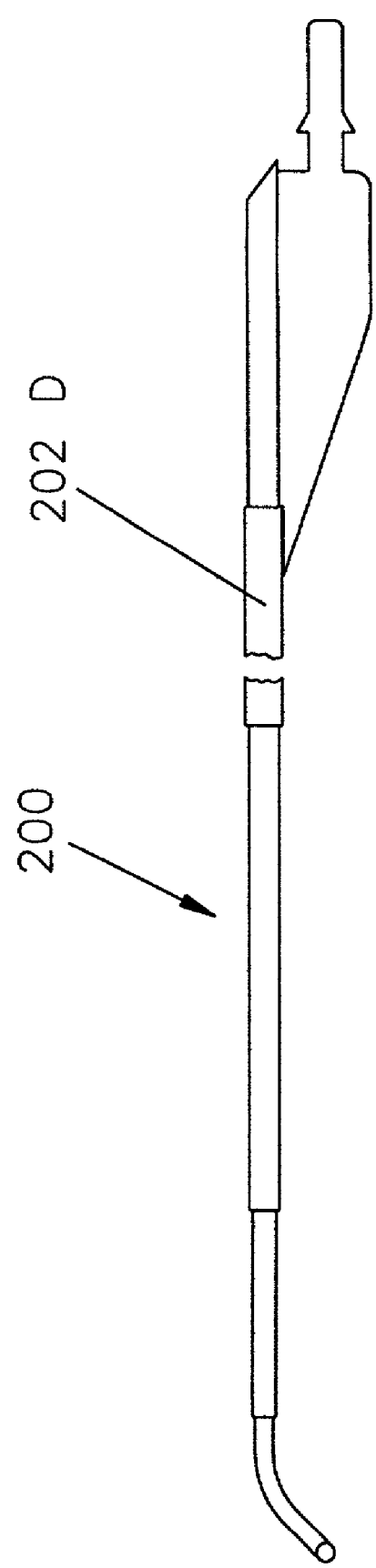

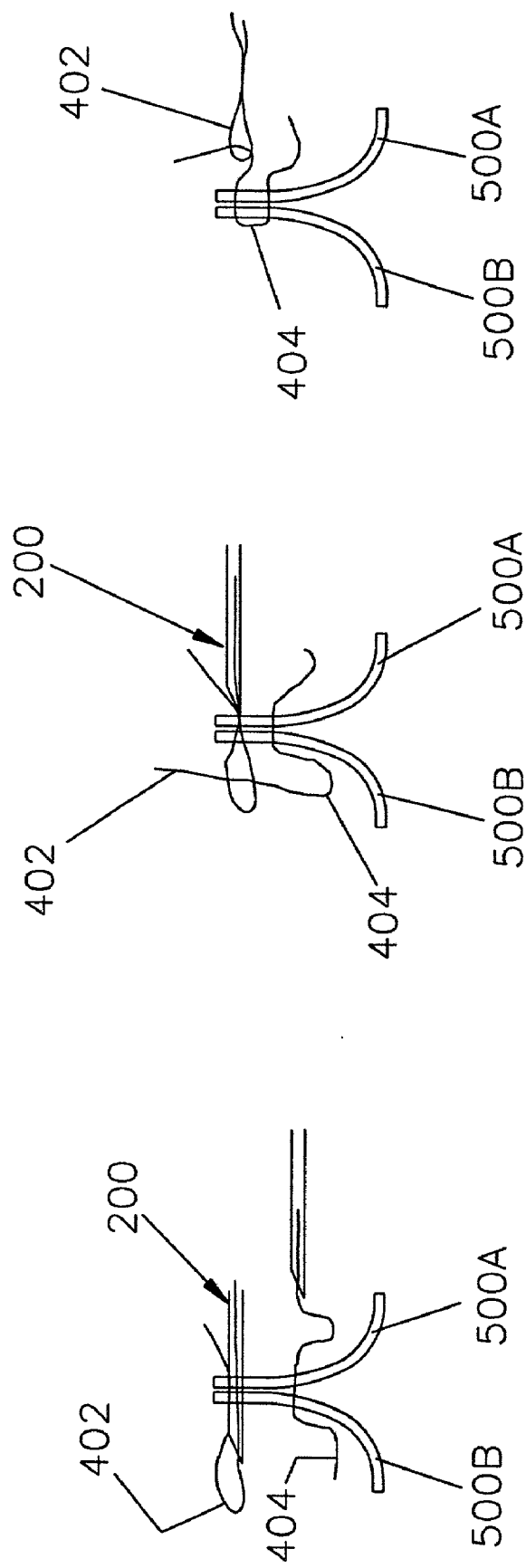

SURGICAL REPAIR KIT AND ITS METHOD OF USE

This is a continuation of U.S. patent application Ser. No. 09/111,237, filed Jul. 7, 1998, now abandoned, by Kwan-Ho Chan for SURGICAL REPAIR KIT AND ITS METHOD OF USE, which in turn is a continuation of U.S. patent application Ser. No. 08/727,027, filed Oct. 8, 1996 now U.S. Pat. No. 5,776,151 by Kwan-Ho Chan for SURGICAL REPAIR KIT AND ITS METHOD OF USE, which is in turn a continuation of U.S. patent application Ser. No. 08/234,840, filed Apr. 28, 1994 now U.S. Pat. No. 5,562,683 by KwanHo Chan for SURGICAL REPAIR KIT AND ITS METHOD OF USE, which is in turn a continuation-in-part of U.S. patent application Ser. No. 08/090,651, filed Jul. 12, 1993 now U.S. Pat. No. 5,562,687 by KwanHo Chan for SURGICAL REPAIR KIT AND ITS METHOD OF USE.

FIELD OF THE INVENTION

The present invention relates to medical devices for performing surgery and a surgical repair kit containing the same. More particularly, the present invention is directed to a surgical repair kit useful for performing arthroscopic meniscal repairs and other surgical procedures.

BACKGROUND OF THE INVENTION

Menisci are tough rubbery "C" shaped cartilage cushions that are attached by ligaments to the top (plateau) of the tibia. They prevent the surfaces of the tibia and femur from grinding against each other and act as the shock absorbers in the knee.

Meniscal tears are a common problem in the United States, especially among amateur and professional athletes. While menisci are also located in the shoulder, the most common meniscus injury occurs in the knee. There are two menisci in each knee. Each year, tens of thousands of people suffer meniscal tears, particularly in or at the site of one or both knees. If these tears are not repaired, there may be a progressive deterioration of the cartilage, leading to the painful rubbing and wearing of bones which had previously been covered by cartilage. This, in turn, leads to inflammatory synovitis, arthritis and other debilitating ailments. Consequently, there are at least 30,000 to 40,000 meniscal excisions or repairs to the shoulder and the knee performed each year.

Men and women between the ages of 18 and 45 experience the majority of meniscal tears, usually during athletic activity, such as when twisting, cutting, pivoting, decelerating or when being tackled. When torn, the meniscus may have a longitudinal, horizontal or radial ("parrot beak") tear.

The damaged meniscus may be diagnosed with the assistance or use of magnetic resonance imaging (MRI) and/or an arthroscopic examination. Arthroscopy enables a surgeon to look into the joint using a miniature video camera. In many cases, torn fragments of the meniscus are removed arthroscopically. In other cases, a small tear at the periphery of the meniscus with a very swollen knee joint may be treated by draining the joint, temporarily restricting the use of the knee, and slowly having the patient begin rehabilitative exercises.

However, in still other cases, the tears in the meniscus do require surgical repair, normally by sewing the torn sections of the meniscus together. The use of the arthroscope greatly aids in the surgical repair of the meniscus by allowing the surgeon to better visualize the small areas between which the torn meniscus lies. The arthroscope enables the surgeon to visualize the interior of the joint and to perform surgery through small puncture holes without having to open the joint as has been done in the past.

A number of surgical tools have been developed to assist in suturing, and in particular the suturing of the meniscus.

U.S. Pat. No. 2,808,055 (Thayer) discloses a surgical stitching instrument which accommodates a bobbin of suture material and include means to feed the suture material to a needle. A slidable thread moving member is provided for advancing the suture material through the needle.

U.S. Pat. No. 3,476,114 (Shannon, et al.) discloses a ligating implement comprising an elongated instrument through which a ligature passes to form a loop at one end with a disc. The disc provides a means whereby the loop may be drawn tight above a severed vessel of the like.

U.S. Pat. No. 3,476,115 (Graeff, et al.) discloses a ligating implement as in Shannon, et al. and includes severing means to prevent overstressing of the locking disc during tightening of the noose.

U.S. Pat. No. 4,493,323 (Albright, et al.) discloses a suturing device and a method for its use in arthroscopic surgery. The suturing device comprises an elongated tube and plunger which are used to hold and advance a pair of needles united by a length of suture material.

U.S. Pat. No. 4,641,652 (Ilutterer, et al.) discloses an applicator for tying sewing threads which comprises a helical tubular coil connected to a shaft having an axial passage. A catcher loop is extendable through the shaft to catch a sewing thread inserted manually into the coil passage.

U.S. Pat. No. 4,935,027 (Yoon) discloses surgical instruments and methods for effecting suturing of tissue controlled from a position remote from the suture site. The invention provides for the continuous feeding of suture material through opposed forcep jaw members between which the tissue segments are interposed.

U.S. Pat. No. 5,112,308 (Olsen, et al.) discloses a medical device for and a method of endoscopic surgery. The device includes a dilator having a tapered end and a central passage which accommodates a guide wire for directing the dilator. This device does not include any means whereby the guide wire may be secured to the dilator or otherwise manipulated in conjunction therewith.

U.S. Pat. No. 4,779,616 (Johnson) discloses a method for snagging an end of a surgical suture during arthroscopic surgery, comprising deploying a distal end of a cylindrical cannula adjacent to the end of the suture within the body and passing a resilient loop through the cannula to snag the suture.

U.S. Pat. Nos. 4,890,615, 4,923,461 and 4,957,498 (Caspari, et al.) discloses a suturing instrument and method of use in arthroscopic surgery. The suturing instrument includes a hollow needle for penetrating tissue to be sutured within the body while the tissue is clamped between relatively movable jaws and a suture feed mechanism for feeding suture material through the hollow needle. The jaws can be opened and the suturing instrument withdrawn from the body, pulling the free end segment of the suture material with the instrument.

SUMMARY OF THE INVENTION

It is an object of the present invention to provide a surgical repair kit. In particular, it is an object of the present invention to provide a surgical repair kit which is particularly suited for the repair of torn menisci.

It is another object of the present invention to provide a suture passer having means for positioning of the suture.

It is another object of the present invention to provide a parallel needle guide to allow for an easier and more successful placement of a second needle in close proximity to the first needle that has been previously inserted in the area of a tissue tear.

Another object of the present invention is to provide a modular suture passer assembly of the sort comprising a handle and a cannula, wherein the handle is adapted to releasably and lockingly hold the cannula for manipulation by a surgeon so that a length of suture may be passed through tissue.

Still another object of the present invention is to provide a surgical kit for use in passing a length of suture through tissue, wherein the kit comprises a handle and various interchangeable cannulas, with each cannula being adapted to be releasably and lockingly held by the handle during a surgical procedure.

Yet another object of the present invention is to provide a surgical cannula having a sharp distal tip which is adapted to pierce tissue.

another object of the present invention is to provide a surgical cannula having a sharp distal tip which is adapted to pierce tissue while at least one strand of suture extends out of the cannula sharp distal tip, wherein the sharp distal tip of the cannula is specially configured to minimize the possibility of damaging or severing the suture during the tissue piercing operation.

Still another object of the present invention is to provide a modular suture passer assembly which is relatively simple to manufacture and relatively easy to use.

Yet another object of the present invention is to provide a new method for passing suture through tissue.

While the present invention is primarily concerned with the repair of torn menisci, the repair kit, the parallel needle guide, and the suture passer may be used in other surgical procedures, e.g. for suturing internal tissue at least partially accessible through a body cavity.

The suture passer of the invention comprises a longitudinally-extending hollow cannula having a central passage slidingly receivable of a surgical suture and a manually graspable handle connected to the hollow cannula for manipulation thereof. The suture passer has a first guide means connected to an upper surface of the handle, proximate to a distal end of the handle for releasably, guidingly holding the surgical suture, and a second guide means connected to the upper surface of the handle, proximal to the first guide means for releasably, guidingly holding the surgical suture.

In one embodiment of the invention, the hollow cannula is connected to the upper surface of the handle and the hollow cannula terminates at a rearward opening between the first and second guide means.

In another embodiment of the invention, the hollow cannula is received within a bore formed in the handle, with the bore terminating at an opening in the upper surface of the handle between the first and second guide means.

The guide means may be loops which are either parallel or transverse to the longitudinally-extending hollow cannula. In an alternative embodiment, the second guide means may consist of a plurality of bent fingers lying in parallel planes.

The guide means serve as means about which the suture is passed so it may be manipulated longitudinally with respect to the cannula. The diameter of the central passage of the cannula is such that the tip of a spinal epidural or similar needle into which the suture is directed may fit into the cannula and is large enough to allow the sliding passage of two surgical sutures (i.e. the two limbs of a single surgical suture). In the method of use, the suture passer is used in surgical manipulations, and in particular meniscal repairs or other arthroscopic procedures to direct a suture within a joint space with a greater degree of precision than available by current methods.

When the two limbs of a surgical suture are within the cannula, the guide means function to separate the two limbs. Separation of the limbs of the surgical suture allows independent manipulation of the suture limbs. Digital manipulation of the surgical suture between the first and second guide means causes longitudinal passage of one limb of the surgical suture within the cannula, i.e. friction between the digit and the said suture will cause the said suture to slide along the top surface of the handle, into or out of the cannula, when manipulated digitally.

In one surgical repair kit formed in accordance with the present invention, the kit comprises a suture passer, as previously described, at least two surgical needles of predetermined length and at least one stylet for each surgical needle. Preferably, the surgical repair kit includes three surgical needles, with one of the surgical needles having a length greater than that of the other needles.

In one preferred embodiment, the suture passer is provided with a metal cannula, and the surgical repair kit includes a cannula bender for bending the metal cannula in a desired manner. The cannula bender comprises a base and a pair of upwardly stepped symmetrical bolsters positioned on top of the base allowing the cannula to be bent to the right or to the left, each step of each bolster having a predetermined radius of curvature wherein the radius of curvature of each step is smaller than the radius of curvature of the step immediately below.

Additionally, in one surgical repair kit formed in accordance with the present invention, the kit may further include a parallel needle guide for guiding the surgical needles for desired placement relative to each other. The parallel needle guide comprises at least three longitudinally extending, hollow tube-shaped units longitudinally adhered to each other, in a plane, parallel to one another, each of the tube-shaped units slidingly receivable of a surgical needle therethrough.

The present invention also provides methods for the suturing of internal tissue which is at least partially accessible through a body cavity.

A first method comprises the steps of:

(A) providing at least one suture having a first limb and a second limb;

(B) providing a suture passer comprising a longitudinally extending hollow cannula having a distal opening, a proximal opening and a central passage slidingly receivable of a surgical suture;

(C) introducing the distal end of the cannula into a body cavity at least partially accessing internal tissue to be sutured:

(D) identifying a first insertion site for passing a first limb of a suture through the internal tissue to be sutured;

(E) inserting a first hollow needle through the first insertion site, the hollow needle extending from outside the body through the first insertion site into the body cavity;

(F) identifying a second insertion site for passing a second limb of the suture through the internal tissue to be sutured;

(G) inserting a second hollow needle through the second insertion site, the hollow needle extending from outside the body through the second insertion site into the body cavity;

(H) passing the second limb of the suture through the first hollow needle into the distal opening of the cannula until it exits the proximal opening of the cannula;

(I) feeding the second limb of the suture back into the cannula through the proximal opening;

(J) passing the second limb of the suture through the hollow cannula into the second hollow needle until it exits the needle external of the body;

(K) drawing the suture through the cannula into the body cavity;

(L) removing the first and second needles by drawing them outwardly of the body cavity;

(M) tying the limbs of the suture; and (N) repeating steps (D)–(M) until a surgically sufficient number of sutures have been tied.

A second method comprises the steps of:

(A) providing at least one suture having a first limb and a second limb;

(B) providing a suture passer comprising a longitudinally-extending hollow cannula having a distal opening, a proximal opening and a central passage slidingly receivable of a surgical suture;

(C) loading the suture passer with a surgical suture such that an end of the first limb of the suture and an end of the second limb of the suture each protrude from the distal end of the cannula;

(D) introducing the distal end of the cannula into a body cavity at least partially accessing internal tissue to be sutured;

(E) identifying a first insertion site for passing the first limb of the suture through the internal tissue to be sutured;

(F) inserting a first hollow needle through the first insertion site, the hollow needle extending from outside the body through the first insertion site into the body cavity;

(G) identifying a second insertion site for passing a second limb of the suture through the internal tissue to be sutured:

(H) inserting a second hollow needle through the second insertion site, the hollow needle extending from outside of the body through the second insertion site into the body cavity;

(I) introducing the end of the first limb of the suture into the first hollow needle until it exits the first hollow needle outside the body;

(J) introducing the end of the second limb of the suture into the second hollow needle until it exits the second hollow needle outside the body;

(K) drawing the suture through the cannula into the body cavity;

(L) removing the first and second hollow needles by drawing them outwardly of the body cavity;

(M) tying the limbs of the suture; and (N) repeating steps (C)–(M) until a surgically sufficient number of sutures have been tied.

In a further modification of the invention, the suture passer may be formed in a modular fashion so that a variety of different cannulas can be attached to its handle. These cannulas may be blunt or sharply pointed, and they may be straight or curved, as required for a particular surgical procedure. In this form of the invention, the suture passer's handle includes a female lock portion which is configured to receive and lockingly hold a cannula which is provided with a corresponding male lock portion.

In a preferred form of the modular suture passer, each of the interchangeable cannulas is provided with a radial fin which is attached to the cannula adjacent to the cannula's proximal end. This fin includes a main portion and a tab portion. The tab portion of the fin extends proximally from the main portion of the fin. The tab portion of the fin includes an upper tab projection defining an upper, distally facing tab shoulder and a lower tab projection defining a lower, distally facing tab shoulder. The tab portion's upper and lower tab projections are located between the main portion of the fin and the proximal end of the tab portion. The tab portion's upper and lower tab shoulders are aligned with one another.

The modular handle includes first and second suture guide means generally of the sort disclosed above.

The modular handle also comprises a first bore which extends proximally and axially into the handle from the distal end thereof. The first bore includes a stop at its proximal end. The first bore is sized and positioned so that it can receive the proximal portion of a selected cannula, with the proximal end of the cannula's central lumen opening onto the upper surface of the handle between the first and second guide means when the cannula's proximal end is in engagement with the first bore's stop. A slot extends proximally and axially into the handle from the distal end thereof. The slot communicates with the handle's first bore and is sized to receive the main portion of the fin of a cannula when that cannula is mounted to the handle.

A cavity is formed in the handle immediately proximal to the slot. This cavity is sized to receive the tab portion of a cannula when that cannula is mounted to the handle. An upper sidewall projection extends inwardly into the cavity from one of the sidewalls of the cavity, and a lower sidewall projection extends inwardly into the cavity from the same sidewall of the cavity. The upper sidewall projection defines an upper, proximally facing sidewall shoulder, and the lower sidewall projection defines a lower, proximally facing sidewall shoulder. The upper and lower sidewall shoulders are aligned with one another. The upper and lower sidewall projections are located such that as the tab portion of a given cannula enters the handle's cavity, the cannula's upper and lower tab projections will snap over and lockingly engage the handle's upper and lower sidewall projections when the cannula is fully inserted into the handle's first bore. In particular, when the assembly is in this locked condition, the cannula's distally facing upper tab shoulder will engage the handle's proximally facing upper sidewall shoulder, and the cannula's distally facing lower tab shoulder will engage the handle's proximally facing lower sidewall shoulder.

When a given cannula has been mounted to the handle in the foregoing manner, rotational movement of the cannula relative to the handle is precluded by the engagement of the cannula's main fin portion with the sidewalls of the handle's slot. In addition, axial movement of the cannula relative to the handle is precluded (i) in the proximal direction by the engagement of the proximal end of the cannula with the stop located at the proximal end of the handle's first bore, and (ii) in the distal direction by the engagement of the cannula's two distally facing tab shoulders with the handle's two proximally facing sidewall shoulders.

The handle of the modular suture passer also includes means for releasing a cannula from its locking engagement with the handle. More particularly, when a given cannula has been mounted to the handle in the foregoing manner, the proximalmost portion of the cannula's tab portion will extend proximally into a second bore formed in the handle. The second bore extends axially through the handle, from the proximal end of the handle's cavity to the proximal end of the handle. A release rod is positioned within the second bore for reciprocal movement therein, between (i) a proximalmost position in which the release rod is withdrawn from engagement with a cannula mounted to the handle, and (ii)

a distalmost position in which the release rod is in engagement with a cannula mounted to the handle. Spring means are provided for yieldably biasing the release rod into its proximalmost position. The release rod has a bevelled distal end terminating a drive surface. A cannula is dismounted from the handle by urging the release rod from its proximalmost position to its distalmost position. As the release rod begins to move from its proximalmost position to its distalmost position, the rod's bevelled distal end will first engage the proximal end of the cannula's tab portion and deflect the tab portion laterally, whereby the cannula's two distally facing tab shoulders will be disengaged from the handle's two proximally facing sidewall shoulders. Thereafter, as the release rod continues to move from its proximalmost position to its distalmost position, the release rod's drive surface will engage the proximal end of the cannula's tab portion, whereby the entire cannula will be driven distally so that the cannula's two tab projections will clear the handle's two sidewall projections. This will unlock the cannula from the handle. The cannula may thereafter be manually withdrawn from the handle by pulling the cannula in a distal direction.

BRIEF DESCRIPTION OF THE DRAWINGS

FIG. 2 is a top view of another embodiment of the suture passer.

FIG. 3 is a side view of the suture passer of FIG. 2.

FIG. 4 is a frontal view of the handle of the embodiment of the surgical suture passer of FIG. 3.

FIG. 32 is a left side view of a modular suture passer formed in accordance with the present invention.

FIG. 33 is a right side view of the modular suture passer shown in FIG. 32.

FIG. 36 is a left side view similar to FIG. 32, except that the modular suture passer's handle is shown in section so as to reveal how the cannula is in locking engagement with the handle.

FIG. 37 is a bottom view similar to FIG. 35, except that the modular suture passer's handle is shown in section so as to reveal how the cannula is in locking engagement with the handle.

FIG. 38 is a left side view similar to FIG. 36, except that the cannula is shown released from its locking engagement with the handle, with the handle's release rod having moved from its proximalmost position to its distalmost position.

FIG. 39 is a bottom view similar to FIG. 37, except that the cannula is shown released from its locking engagement with the handle, with the handle's release rod having moved from its proximalmost position to its distalmost position.

FIG. 40 is an enlarged left side view, partially cut away, of a cannula suitable for use with the modular suture passer shown in FIGS. 32–39.

FIG. 41 is a rear view of the cannula shown in FIG. 40.

FIG. 42 is a top view, partially cut away, of the cannula shown in FIG. 40.

FIG. 43 is an enlarged top view of the pointed distal end of the cannula shown in FIG. 40.

FIG. 44 is an enlarged left side view, partially cut away, of another cannula suitable for use with the modular suture passer shown in FIGS. 32–39.

FIG. 45 is an enlarged left side view, partially cut away, of still another cannula suitable for use with the modular suture passer shown in FIGS. 32–39.

FIG. 48 is an enlarged left side view, partially cut away, of yet another cannula suitable for use with the modular suture passer shown in FIGS. 32–39.

FIG. 49 is an enlarged left side view, partially cut away, of still another cannula suitable for use with the modular suture passer shown in FIGS. 32–39.

FIGS. 62–64 illustrate how a simple stitch can be converted to a mattress stitch with a suture loop using the present invention.

DETAILED DESCRIPTION OF THE PREFERRED EMBODIMENTS

Figure 1:
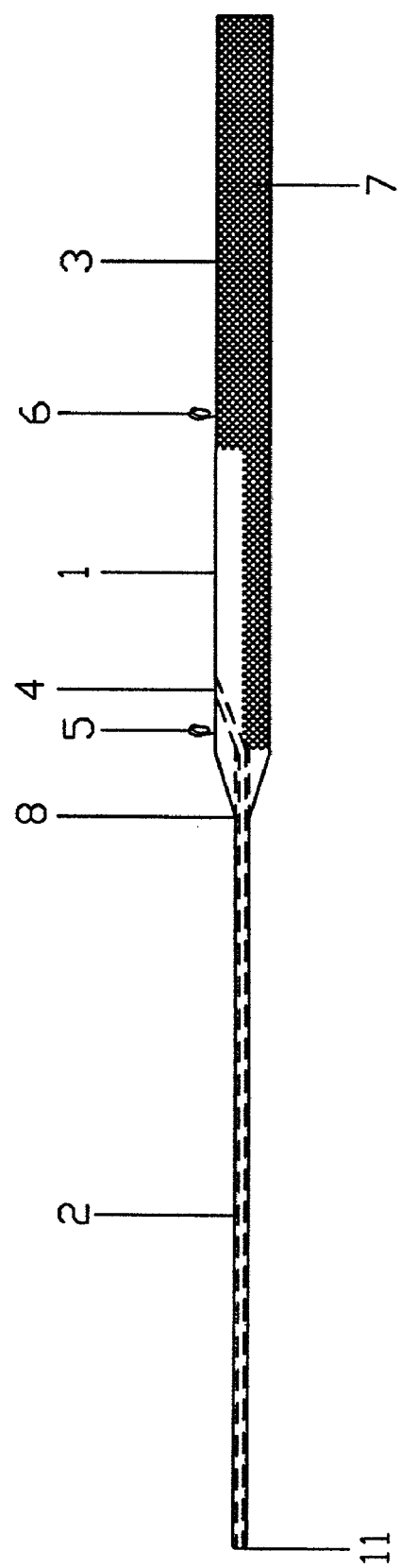
FIG. 1 is a side view of the suture passer.

FIGS. 1–7 illustrate the meniscal suture passer 1, used for the passage of a suture in a confined area of the body during surgery. The suture passer 1 comprises a longitudinally extending hollow cannula 2 having a central passage slidingly receivable of a surgical suture, and a manually graspable handle 3 connected to the hollow cannula 2 for manipulation thereof. A first guide means is connected to the upper surface of the handle 3 for releasably, guidingly holding the surgical suture. A second guide means for guidingly holding the suture, is also connected to the upper surface of the handle 3. The second guide means is proximal to the first guide means. The suture passer 1 in FIGS. 1–6 comprises the cannula 2, the handle 3, a rearward opening 4 near the distal end of the handle 3, a distal loop 5, and a proximal loop 6. The distal loop 5 serves as the first guide means, and the proximal loop 6 serves as the second guide means. Distal loop 5 preferably comprises a single turn open wire loop having a first axis of rotation of the loop and proximal loop 6 is preferably a 1½ pigtail open wire loop having a second axis of rotation of the loop. The loops 5, 6 are preferably parallel to one another. In one embodiment, the wire loops 5 and 6 are preferably perpendicular to the handle 3 with the first axis of rotation and the second axis of rotation transverse to said longitudinally extending hollow cannula 2. In another embodiment, the axes of rotation of loops 5 and 6 are parallel to the longitudinally extending cannula 3. Near the distal end of the handle there is the opening 4 which leads from the handle 3 to the cannula 2. The handle preferably is provided with gripping means and preferably is knurled at 7, so that the surgeon has a better grip on the suture passer 1.

The cannula 2 may be attached and enter through an opening at the concentric center of the handle 3 as shown in FIG. 1. The hollow cannula 2 is received within a bore 8 formed in the handle 3 with the bore 8 terminating at the opening 4 in an upper surface 9 of the handle 3 intermediate the first and second guide means. In an alternative embodiment, the cannula may be connected to the upper surface 9 of the handle 3, as shown in FIG. 3. In this embodiment of the invention, there is no opening into or through the handle 3. Instead, the hollow cannula 2 terminates at a rearward opening 10 between the first and second guide means directly on top of the handle 3. Additionally, in the embodiment of FIG. 1, the handle of the suture passer is rounded, whereas in the embodiment of FIGS. 3 and 4, the suture passer handle 3 is flattened on the side upon which the cannula 2 resides. Additionally, in the embodiment of FIG. 3, the distal loop 5 resides on the cannula 2 just prior to the proximal opening 10 of the cannula 2.

The central passage of the cannula should have a diameter large enough to allow sliding passage of two surgical sutures therethrough. A distal opening 11 of the cannula should also have a diameter large enough to allow engagement with the tip of the spinal or epidural needle for the purpose of passage of the suture between the cannula and the needle.

In the embodiment of FIG. 1, the cannula 2 from its distal opening 11 to the point at which it enters the handle ranges in lengths from about 6.0 cm to about 20.0 cm, and preferably is about 12.0 cm in length. The opening of the cannula 2 is preferably from about 0.08 cm to about 0.32 cm in width, and preferably is about 0.16 cm in width. The wall of the cannula 2 is preferably from about 0.01 cm to about 0.05 cm in thickness, and more preferably is about 0.0254 cm in thickness. The handle preferably has a width ranging from about 0.64 cm to about 1.28 cm, and more preferably is about 0.96 cm in width.

Figure 5:
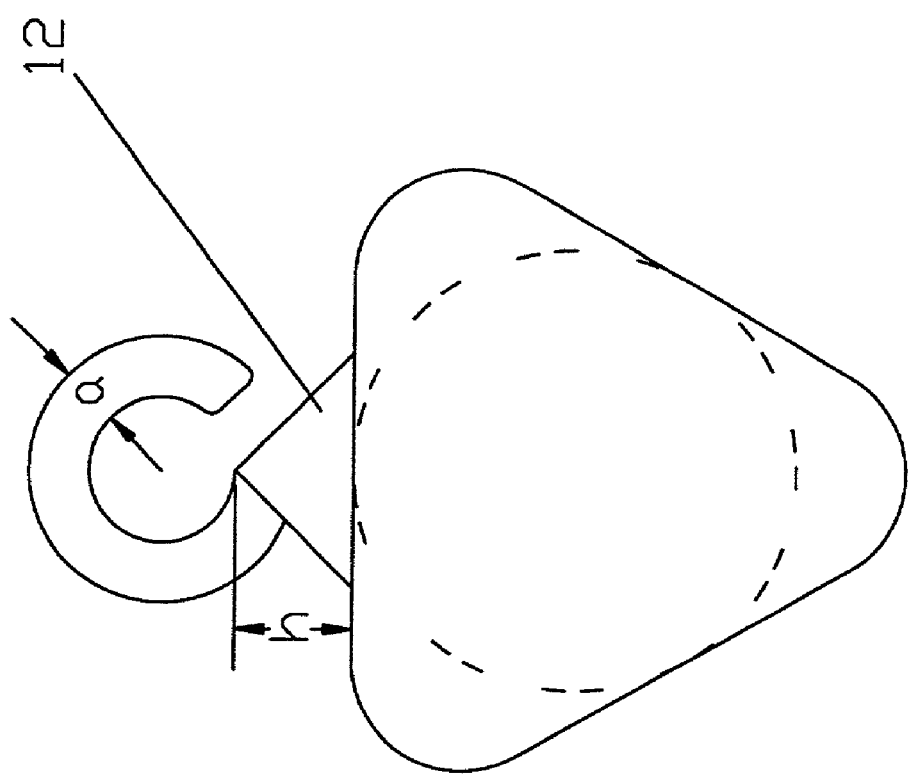
FIG. 5 is a cross section of the handle of the surgical suture passer.

The wire of the wire loops as shown in FIG. 5 ranges from about 0.10 to about 0.14 cm in diameter "a" and preferably is attached to the handle by a mounting structure 12 about 0.1 to about 0.4 cm in height "h".

Figure 6:
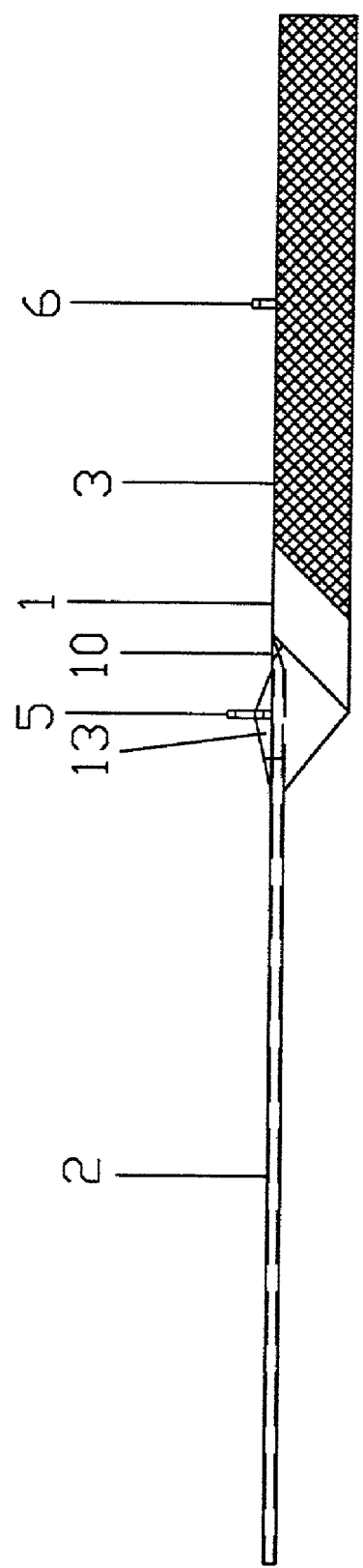
FIG. 6 is a side view of another embodiment of the surgical suture passer.

In the embodiment of the invention illustrated in FIG. 6, the suture passer 1 is similar to the invention illustrated in FIG. 3; however, the cannula 2 is flush with the flattened surface of the handle 1 bearing the wire loops 5 and 6. A segmented piece 13 upon which the distal loop 5 resides attaches the cannula 2 to the handle 3. The proximal opening 10 of the cannula opens on near the proximal side of the segmented piece 13.

In all of the embodiments of the meniscus suture passer 1, the proximal loop G may be fitted anywhere along the length of the handle. However, it is preferable that the proximal loop 6 be fitted about halfway between the ends of the handle of the suture passer.

Figure 7B:
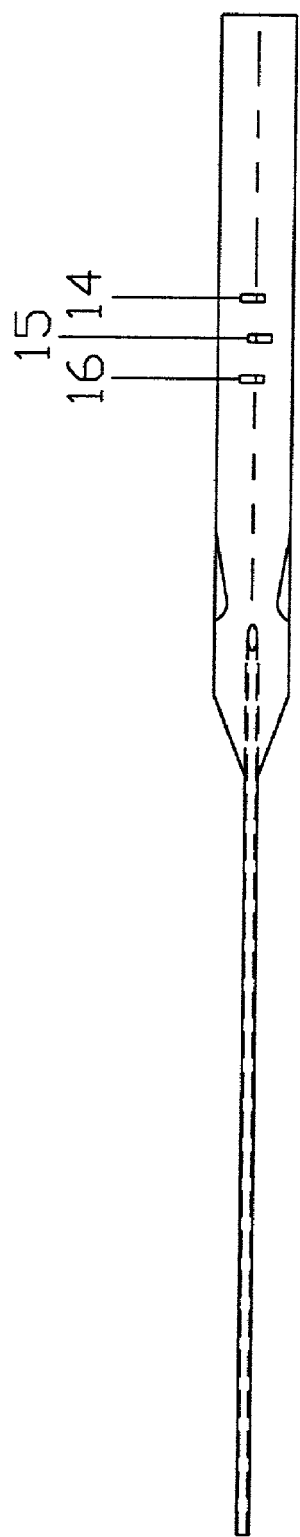
FIG. 7A is a side view and FIG. 7B is a top view of another embodiment of the surgical suture passer.
Figure 7A:
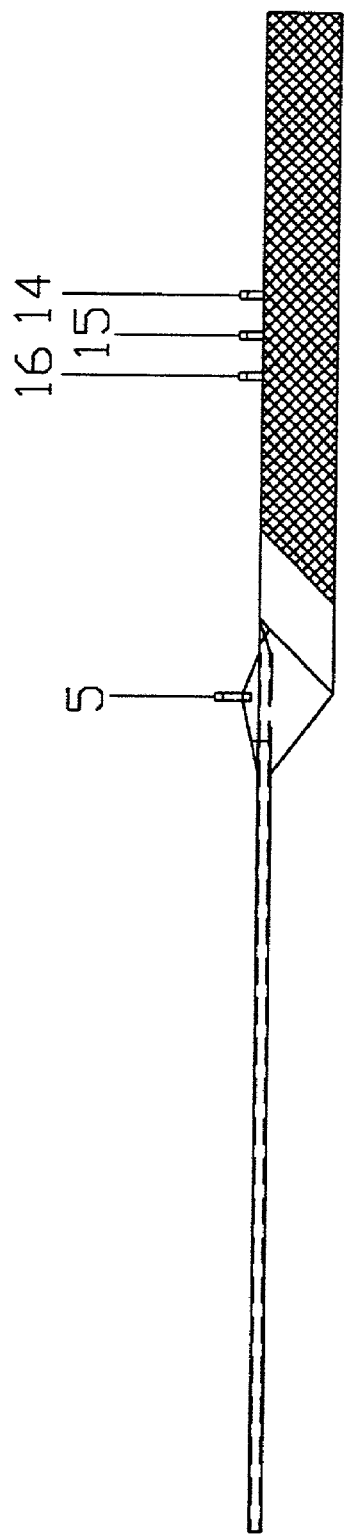

In yet another embodiment of the invention, shown in FIG. 7A and FIG. 7B, the first guide means comprises a single turn open loop lying in a first plane, with the first plane disposed perpendicularly to the longitudinally extending hollow cannula, and a second guide means comprises a plurality of bent fingers lying in parallel planes. The planes are parallel to each other and are perpendicular to the longitudinally extending hollow cannula. The bent fingers may be alternately bent in opposite directions. As shown in FIGS. 7A and 7B, the second guide means may have 3 bent fingers 14, 15, 16.

The suture passer 1 may be made out of either plastic or metal, or a combination thereof, with the handle, loops, or cannula being plastic, metal or any combination thereof. The cannula of the meniscal suture passer may be semi-rigid. The cannula should be rigid enough to stabilize the inner tear of the meniscus during the insertion of the spinal or epidural needle. Additionally, if made of plastic, the cannula should be malleable enough that it can be bent by hand without the need of a special bender. After the cannula is bent it should not spring back. Because of its malleable characteristics, the plastic material is less likely to damage the articular surface. If the suture passer is entirely made out of plastic, the entire suture passer device can be injection molded as a single unit. If the handle is made out of plastic material, the loop or the finger projections may be molded as an integral part of the handle.

If the suture passer is made out of metals, however, the loops may be screwed, riveted, or soldered onto the handle of the suture passer.

Frequently, surgical instruments and suturing devices must be adaptable to the environment or conditions in which they are being used. More specifically, because of the location of the menisci in the shoulder and in the knee, or because there is limited space in that part of the body being repaired for the placement of surgical tools, especially during suturing, it is frequently advisable to adjust the shape of the cannula of the suture passer or to bend the needles being used during suturing the allow for the positioning of the instruments into or through the surgical incision to allow for maximum visibility on the part of the operating team and to avoid crowding of the incision area which would hinder the operating team.

Preferably included in the surgical repair kit when the cannula is made out of metal is a cannula bender. The cannula bender may be used to bend the cannula without kinking the cannula.

Figure 12:
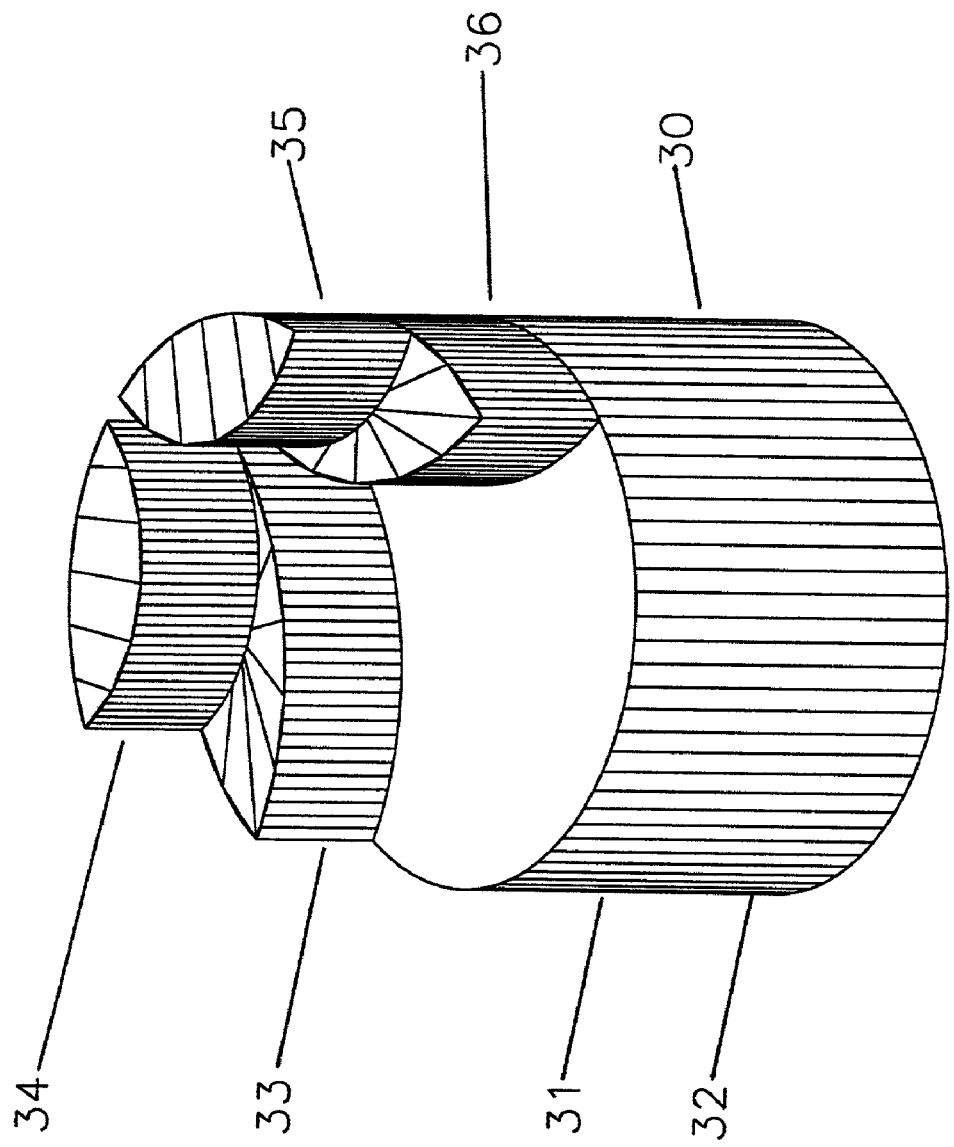
FIG. 12 is a frontal view of a cannula bender.
Figure 13:
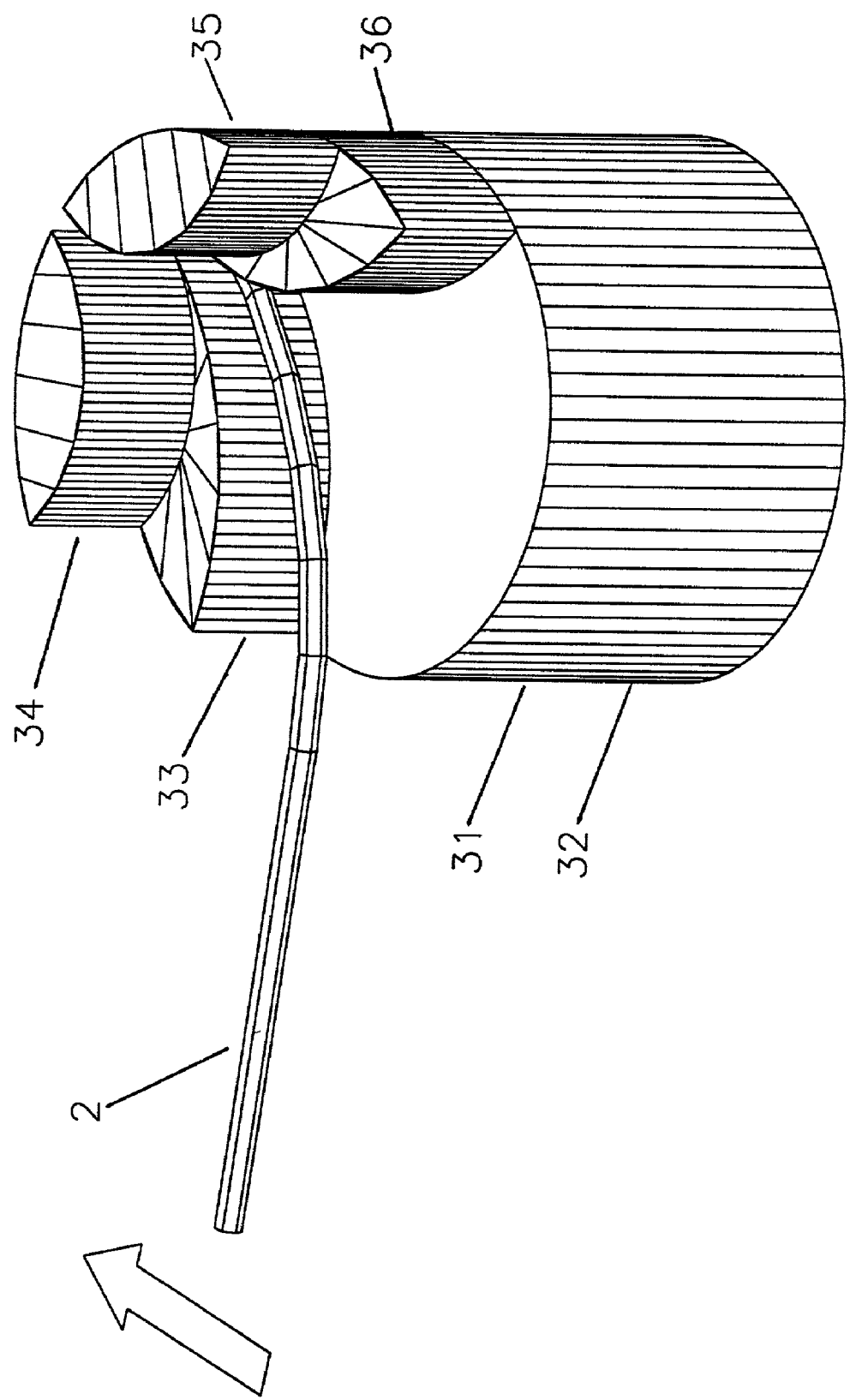
FIG. 13 is a frontal view illustrating the use of the cannula bender.

The cannula bender 30 shown in FIGS. 12 and 13 is designed to bend a cannula to a desired curvature. It is different from the existing tube or cannula benders in that it allows the cannula be bent to various radii of curvature. The cannula bender 30 can also bend the cannula in more than one plane.

A cannula bender 30 shown in FIGS. 12 and 13 is designed to bend a cannula to a desired curvature. It is different from the existing tube or cannula benders in that it allows the cannula be bent to various radii of curvature. The cannula bender 30 can also bend the cannula in more than one plane.

There are symmetrical curved bolsters having steps 33, 34, 35, and 36 on top of the base. The stepped configuration provides the higher steps 34, 35 with a smaller radius of curvature. The steps range from about 0.6 cm to about 4 cm in height, with a preferred height of about 1 cm. (Two steps are illustrated but more can be provided).

The cannula 2 is bent against tie bolsters 33 or 36 to create the desired curvature. If a greater degree of curvature,is required the cannula may be bent against the higher bolsters 34 or 35 that have a smaller radius. The symmetry of the bolsters allows the cannula to be bent to the right or to the left without having to rotate the cannula bender. This allows for a faster, easier use of the cannula bender should the need arise during surgery.

The cannula can be bent again in a different plane by rotating the cannula while maintaining the cannula bender in the same orientation. The pre-bent cannula can be contoured against the bolster in a second plane as long as the curvature is less than the height of the step of the bolster.

The entire cannula does not save to be bent, if at all. The purpose of bending the cannula is for the convenience of the surgeon in passing the suture to and from the needle(s) to the suture passer, and to manipulate the suture passer, to each an area in the cavity or joint that would otherwise be inaccessible by a straight cannula.

Figure 8B:
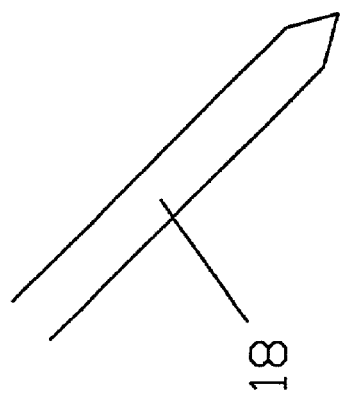
FIG. 8A is an enlarged side view of a tip of a spinal needle and FIG. 8B is an enlarged side view of a tip of an epidural needle.
Figure 8A:
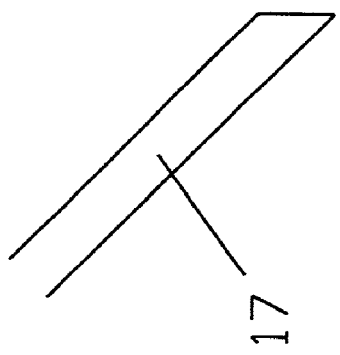

In addition to the suture passer device, the surgical repair kit also contains at least two and preferably three needles. These needles can be either epidural needles or spinal needles. It is preferred that the needles be epidural needles 18, two of which are of the same length, e.g., about 3.5 inches in length and one of which is longer, e.g. about 4.75 inches in length. It is also preferred that the needles be 18 gauge needles. As seen in FIG. 8A, a spinal needle 17 has a bevelled tip which, during repair of the meniscus, may accidentally lacerate the articular cartilage. In contrast, as seen in FIG. 8B, the epidural needle 18 has a Huber tip. With the epidural needle it is easier to advance the needle through tough tissue by using a twisting motion. The "rounded" tip of the epidural needle is less likely to lacerate the articular surface.

Figure 10:
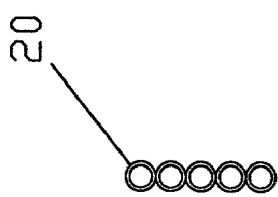
FIG. 10 is a frontal view of a parallel needle guide.
Figure 9:
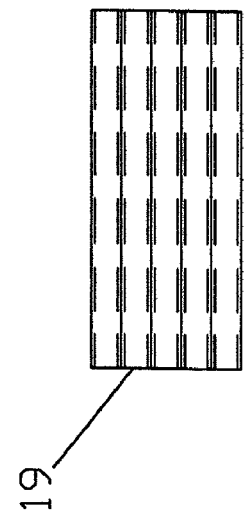
FIG. 9 is a side view of a parallel needle guide.

The surgical repair kit preferably comes with at least two needles of the same length because the needle which is inserted first becomes blunt after several insertions. The insertion of the second, generally longer, epidural needle is easier with the use of the parallel needle guide 19 as shown in FIGS. 9 and 10. (Longer and shorter needles are utilized to prevent the hubs 29A of adjacent needles from interfering with one another by staggering the hub distance from the patient's body). The parallel needle guide allows for the proper alignment of the needles through which the suture will pass. The parallel needle guide is a series of at least three, and preferably four to five hollow tube shaped units 20 longitudinally adhered to each other one on top of the other in a parallel formation. The opening or diameter of each tube shaped unit should be large enough to allow for the passage of an 18 or 21 gauge needle to pass through. The parallel needle guide may be made out of plastic, paper or metal. The parallel needle guide may be from a mold, or the individual tubes may be individually formed and bonded to each other. Any method of forming the structure is acceptable.

Figure 11:
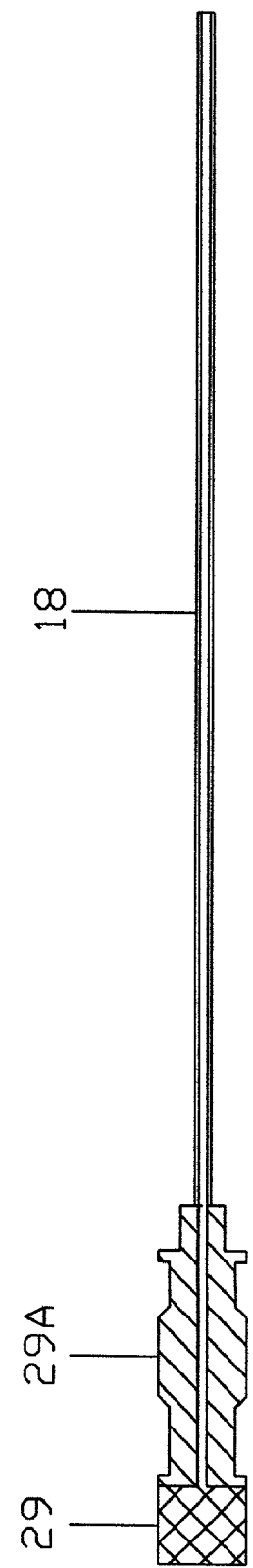
FIG. 11 is a side section view of a needle containing a stylet.

Additionally, there is at least one stylet typified by stylet 29 shown in FIG. 11 in the surgical repair kit for each needle included in the repair kit. The stylet is kept on the needle until the needle is passed through the meniscus. This prevents the needle(s) from being clogged with tissue and cartilage as it is pushed through the cartilage. A needle clogged with tissue will, of course, not allow the suture to be passed through the needle to the suture passer.

A template (not shown) is preferably included in the surgical repair kit. This template, which may be printed on the back of the surgical repair kit container, may be printed on a paper guide inside the meniscal repair kit, or may be provided on, or as, a plastic guide. The template is used as a guide for the bending of the cannula.

Each of the items included in the surgical repair kit is sterile. Additionally, each item in the surgical repair kit is preferably individually packaged in sterile plastic, paper, metal foil, or combinations there.of The packaging should be easy to open, so that the contents thereof are not damaged or do not fall on the operating floor while opening. The content of the package and the packaging may be sterilized with ethylene oxide or by radiation, or any other conventional method for the sterilization of packaged elements.

The surgical repair kit which includes the suture passer, at least two surgical needles of predetermined length, and at least one stylet for each needle, may also contain an optional third needle of greater length than the other two needles, the parallel needle guide, and a template. If the cannula is made of metal, a cannula bender may be included in the repair kit. While the repair kit may be used for any surgery, the repair kit is extremely useful in meniscal repair.

Figure 14:
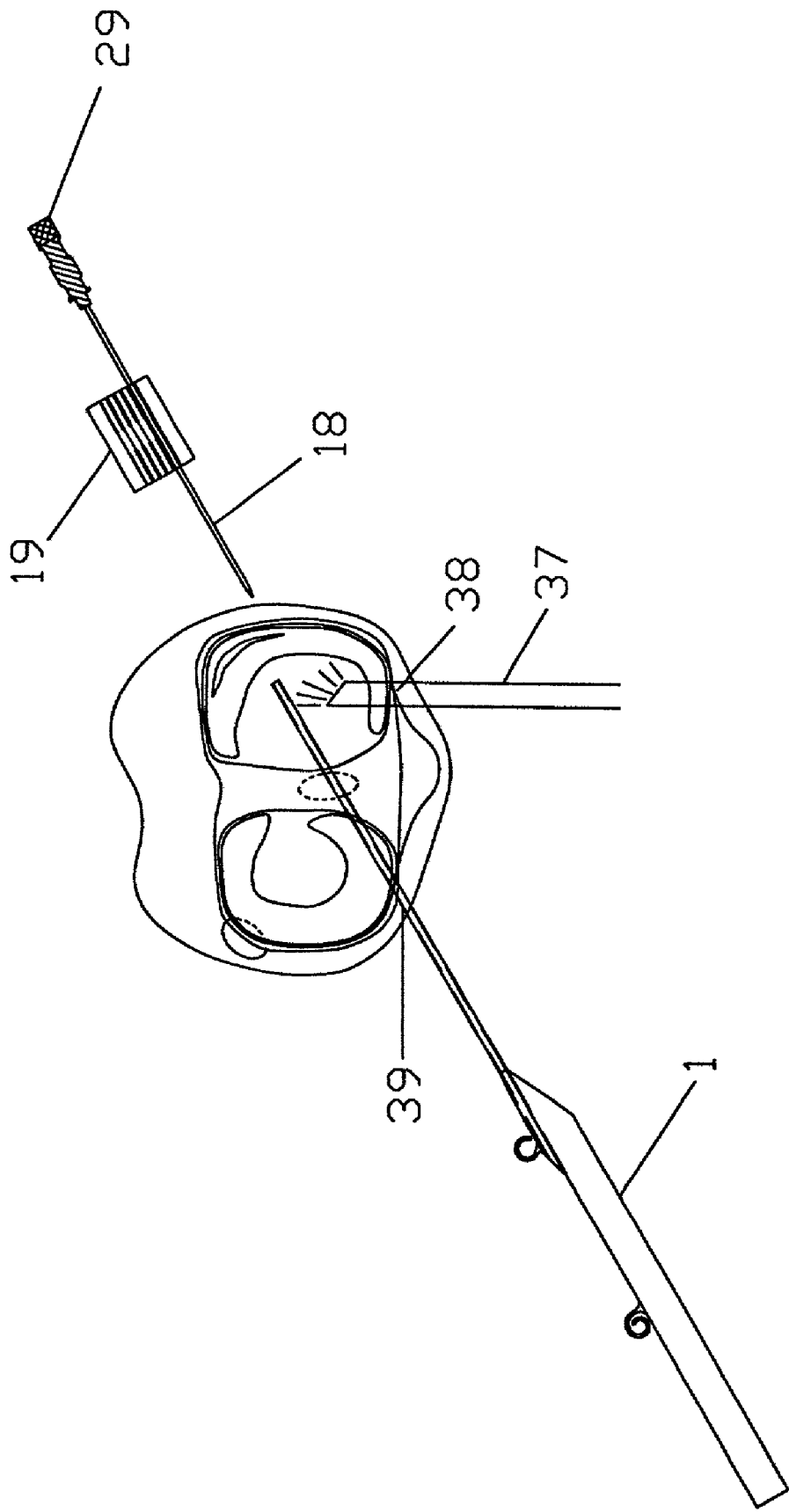
FIG. 14–FIG. 26 are cross-sectional top views at various stages of an operation where the middle third of the meniscus is being repaired.

In repairing the middle third of the meniscus, an arthroscope 37 should enter through the ipsilateral portal 38 as shown in FIG. 14. The suture passer 1 should enter through the contralateral portal 39. The epidural needle is loaded through the hole on one end of the needle guide using a one handed technique to avoid accidental puncture of the surgeon's opposite hand.

There are three methods of identifying the insertion points for the needles.

The first method is to view the meniscal tear with the arthroscope, with the synovial meniscal junction in view, and then advance the arthroscope to the synovial meniscal junction. The light from the arthroscope will transilluminate the skin. The point of insertion of the epidural needle should be slightly distal to this light.

The second method of determining where to insert the needles is to view the meniscal tear and to keep the synovial meniscal junction in view while palpating along the joint line with a tip of a finger or a meniscal probe. The area of maximal wall motion at the synovial meniscal junction indicates the point at which the epidural needle should be inserted.

The third method is the easiest method in determining the needle insertion point, if the synovial meniscal junction is accessible to the suture passer. The tip of the suture passer is pushed against the synovial meniscal junction and the skin is palpated, with the finger. The area of the tip will indicate the approximate location where the needle should be inserted.

Figure 15:
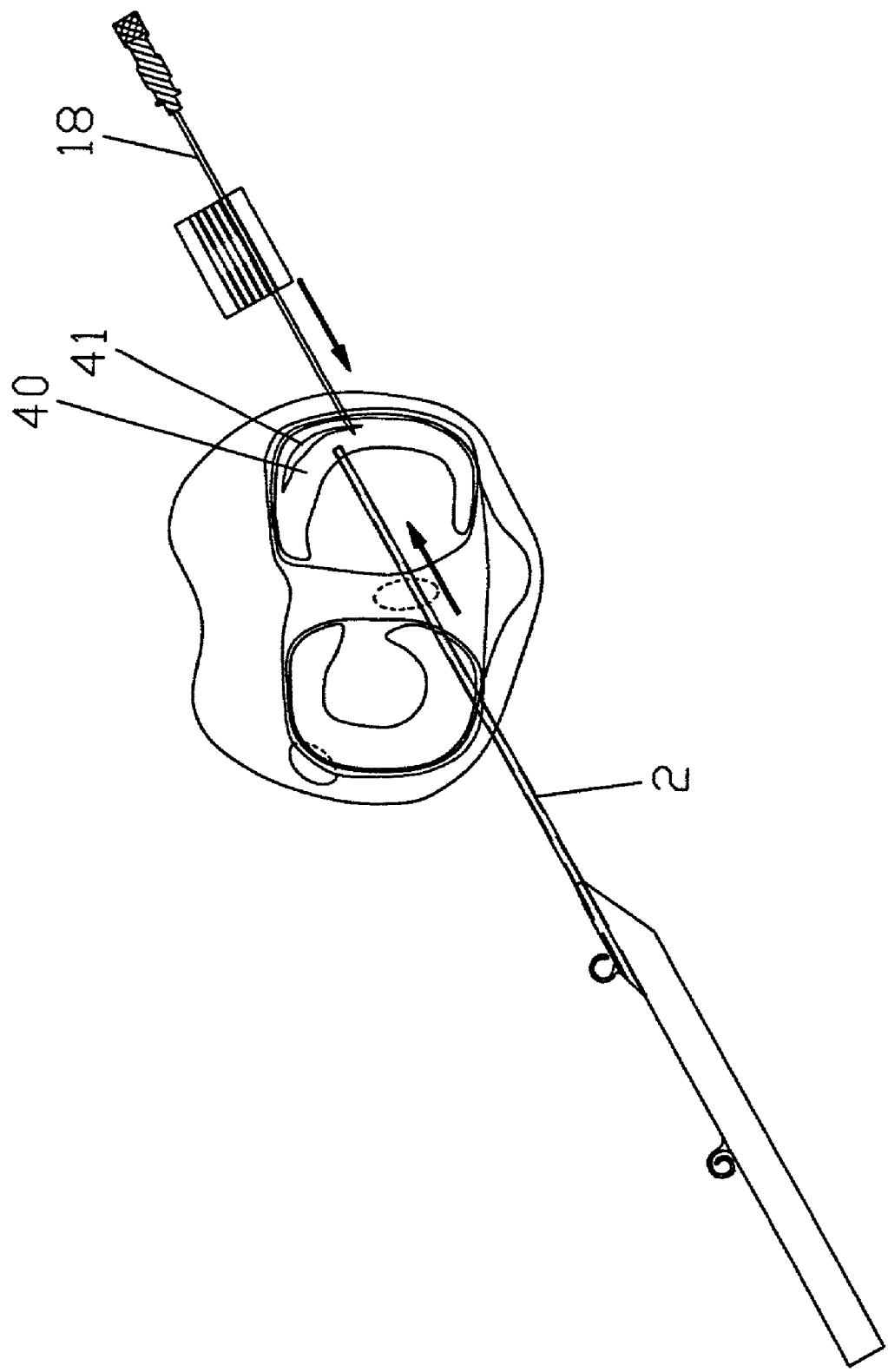

The needles may be advanced with a twisting motion if difficulty is encountered in penetrating the tough meniscal tissue. As shown in FIG. 15, an inner rim 40 of a meniscal tear 41 may be buttressed with the tip of the cannula 2 of the suture passer to stabilize it against the advancing needle 18.

Figure 16:
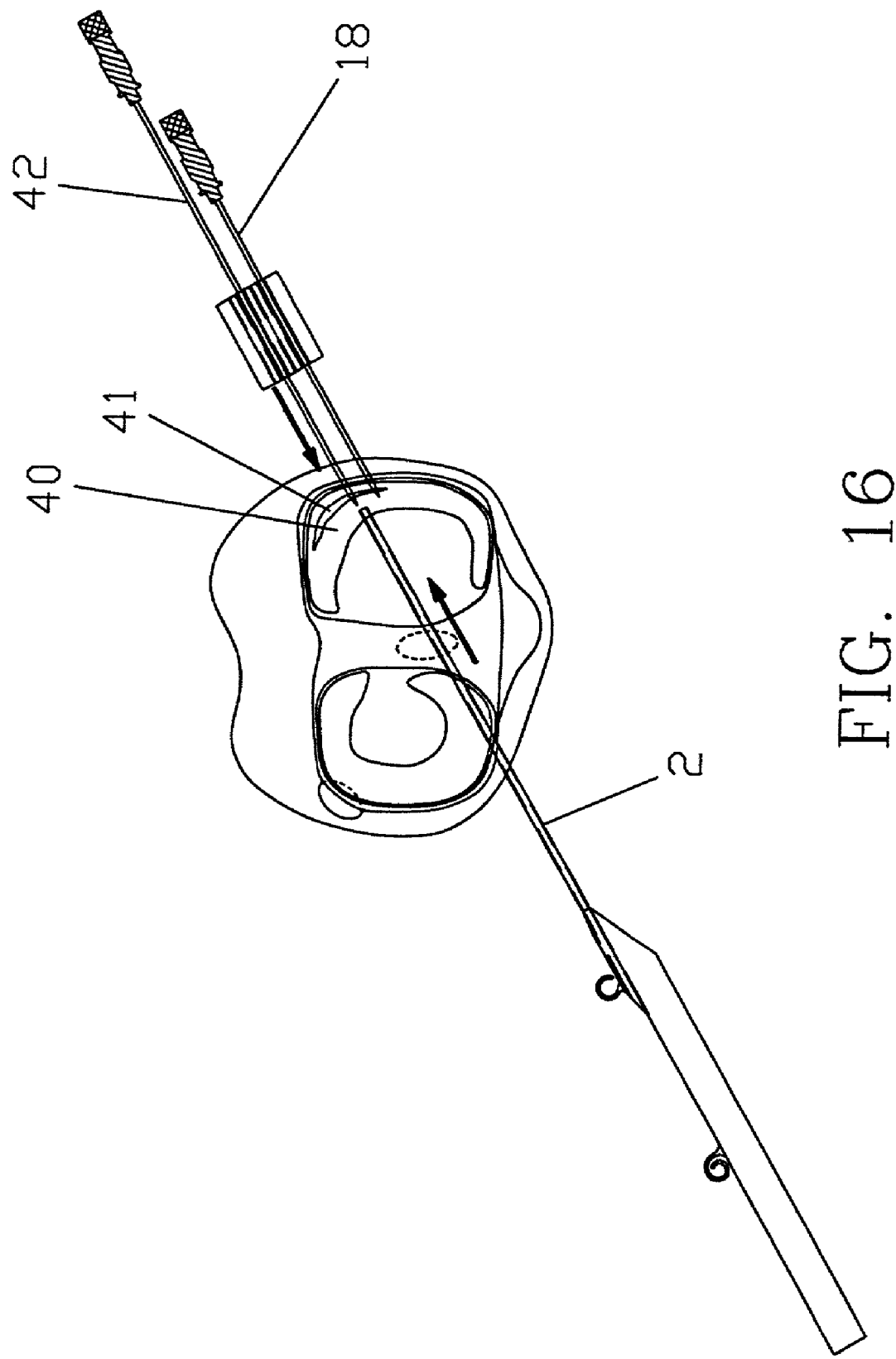

Using the parallel needle guide, two epidural needles are inserted through the guide and across the meniscal tear with a long epidural needle 42 being inserted through the needle guide at a desired separation distance from the shorter needle (as shown in FIG. 16). This longer needle is inserted through the meniscal tissue, preferably behind the shorter needle. The stylets are removed from the needles. A suture is passed through the "first" needle. The tip of the cannula of the suture passer is introduced into the joint cavity through a small incision. The distal opening of the cannula is placed at or near the opening of the needle through which the suture has been passed. There are areas in the joint cavity, although visible through the arthroscope which are not accessible with a straight cannula. Consequently, prior to the introduction of the suture passer, the cannula of the suture passer may be bent on the cannula bender. The curved cannula allows the surgeon to reach remote areas where the meniscus is being repaired.

Figure 17:
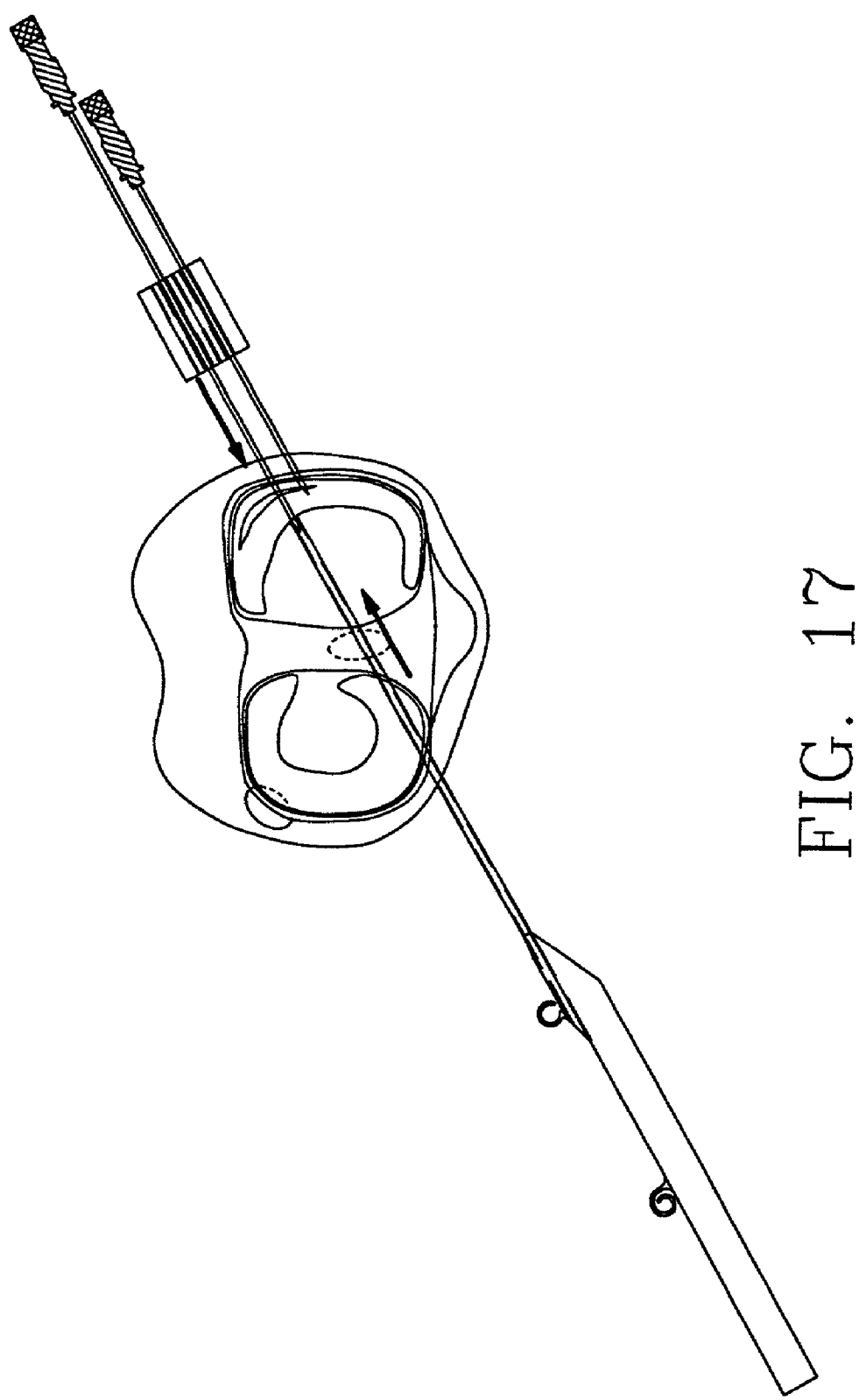

In a preferred method for passing the suture from the cannula to the needle, the needle, preferably an epidural needle with a Huber tip, engages the opening of the cannula (FIG. 17). The more posterior needle is advanced into the joint and the surgeon captures the tip of the needle with the tip of the cannula. For ease of passage, it is preferable that the cannula and needle meet at about a 15°–20° angle. The opening of the needle should be facing away from the apex of engagement between the cannula and the needle. The suture is passed directly from the cannula into the tip of the needle or vice versa.

Figure 18:
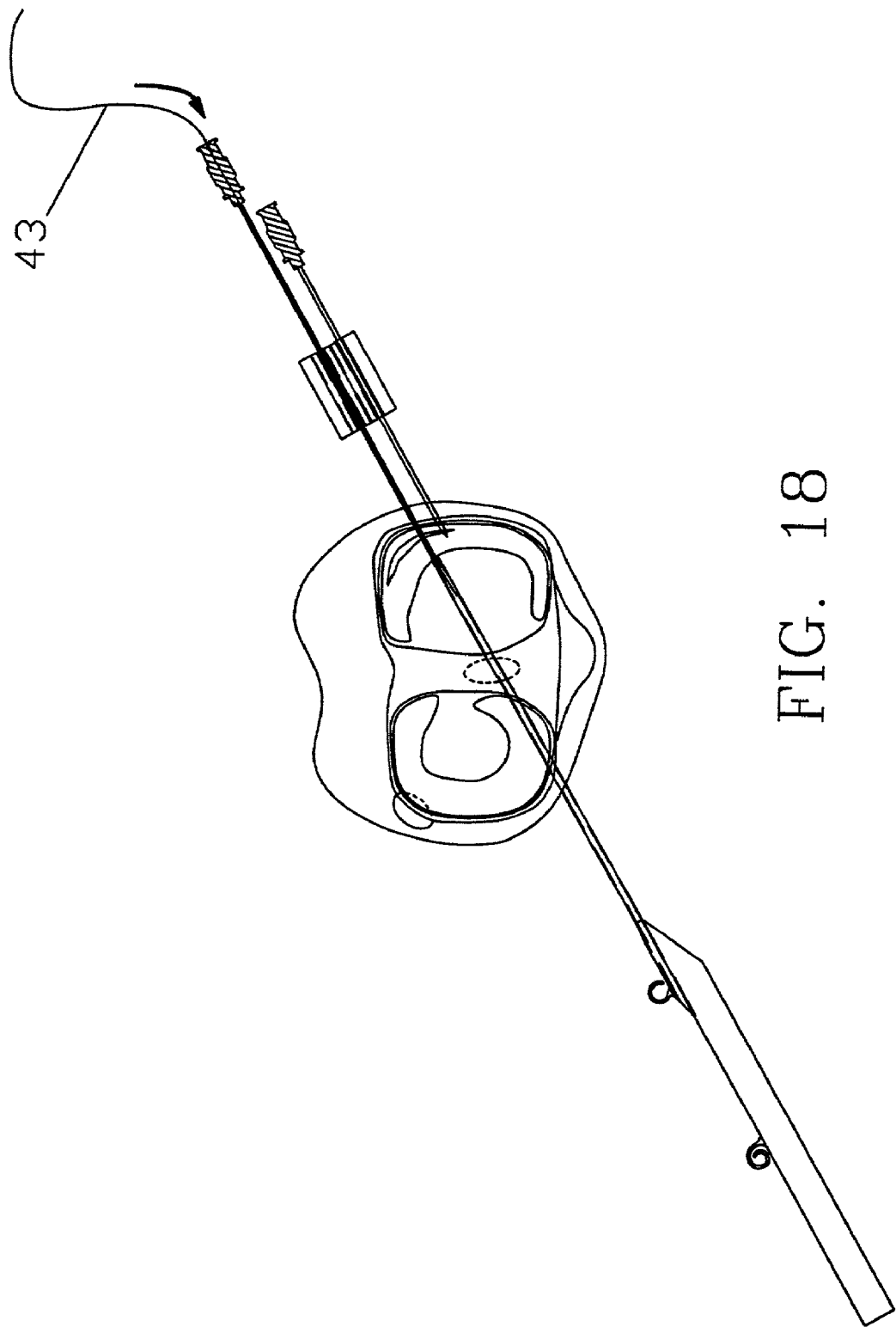
Figure 19:
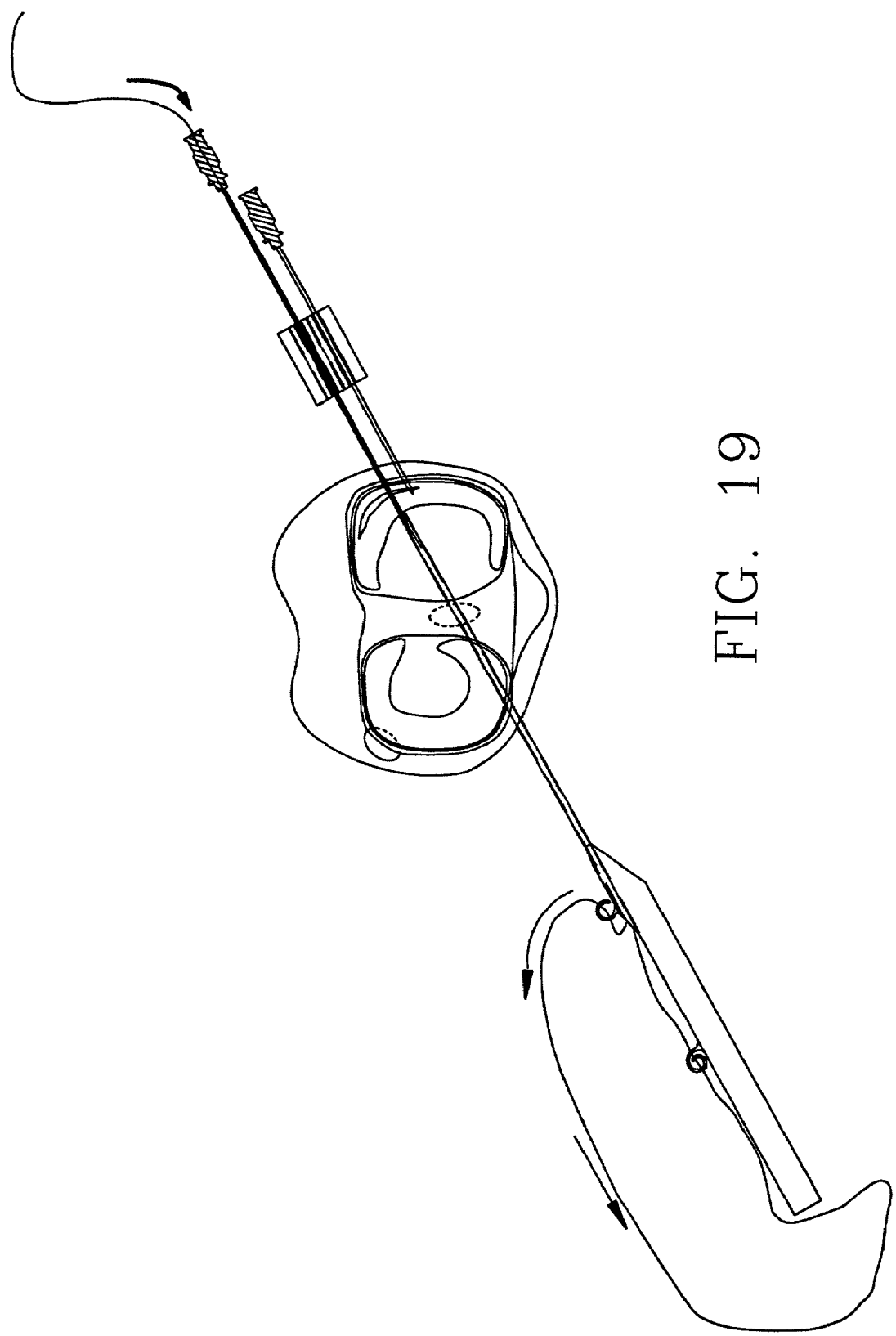

By careful manipulation, the suture 43 is fed through the needle and into the cannula. With the tip of the cannula and the needle securely engaged, the suture is fed (FIG. 18) into the hub of the needle until it exits the proximal end of the cannula at the handle of the suture passer. It is advisable to pull the suture three quarters of the way through. The suture is then looped onto the distal guide and is threaded back into the cannula. The suture is then engaged onto the proximal guide (FIG. 19).

Figure 20:
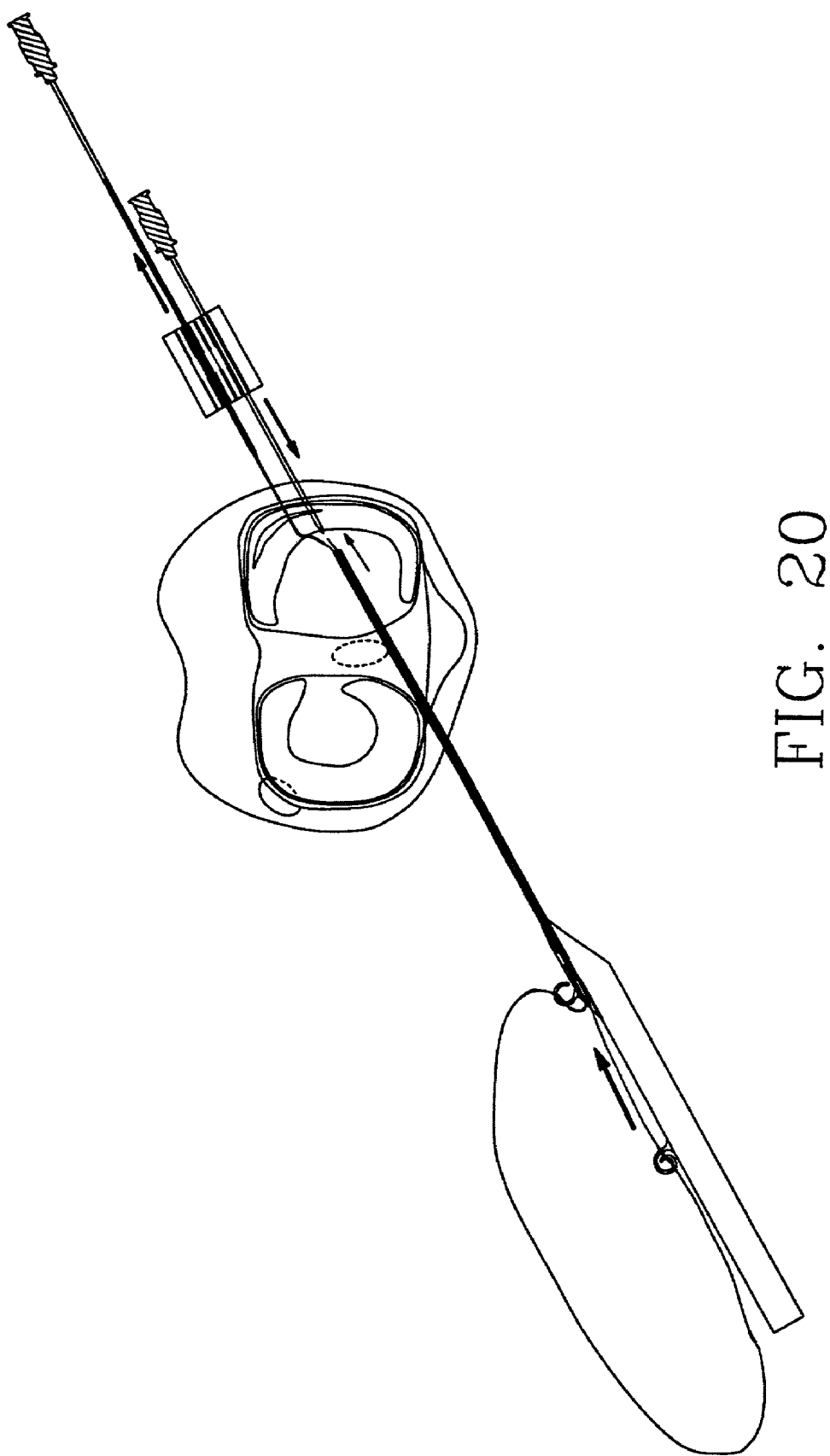
Figure 21:
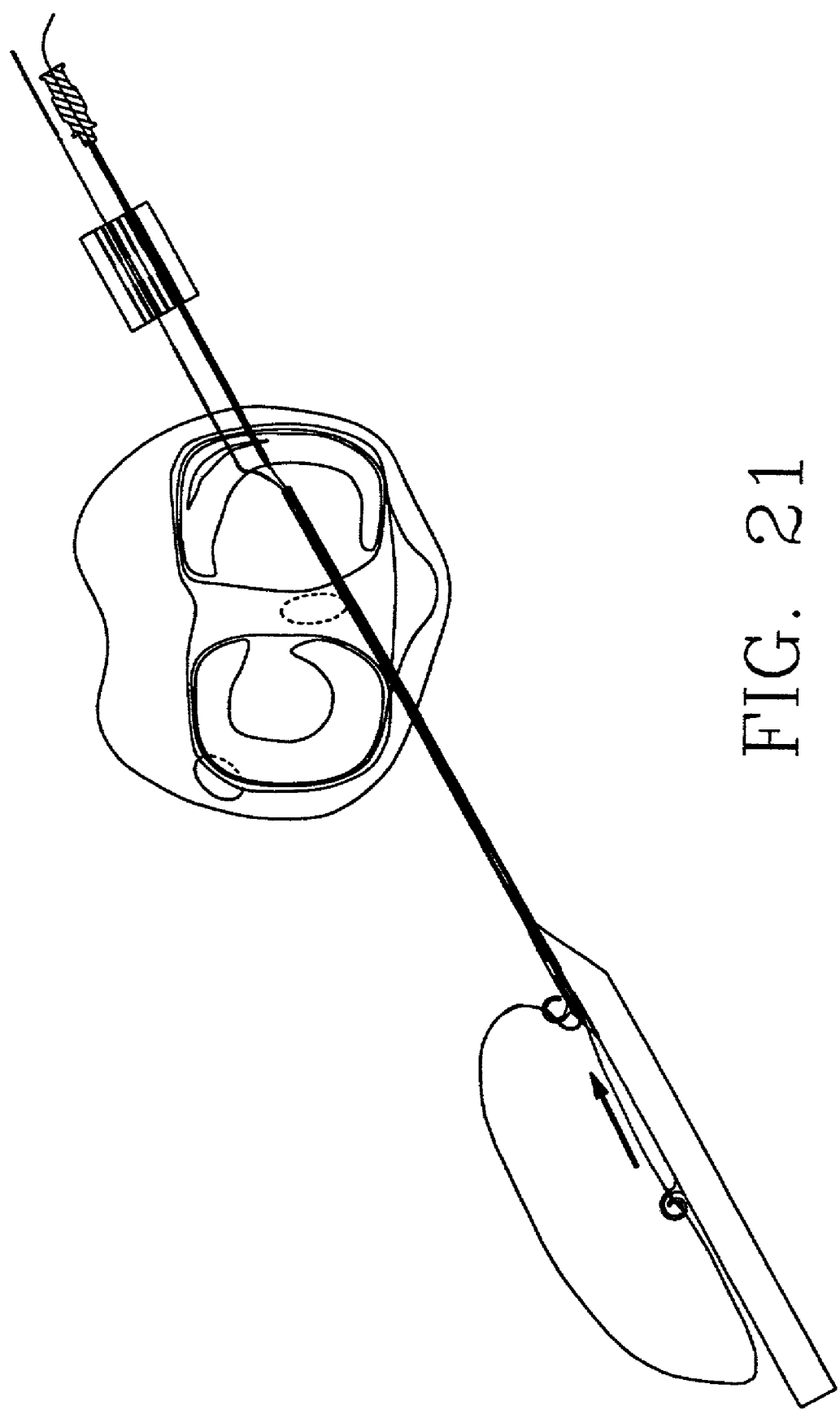
Figure 22:
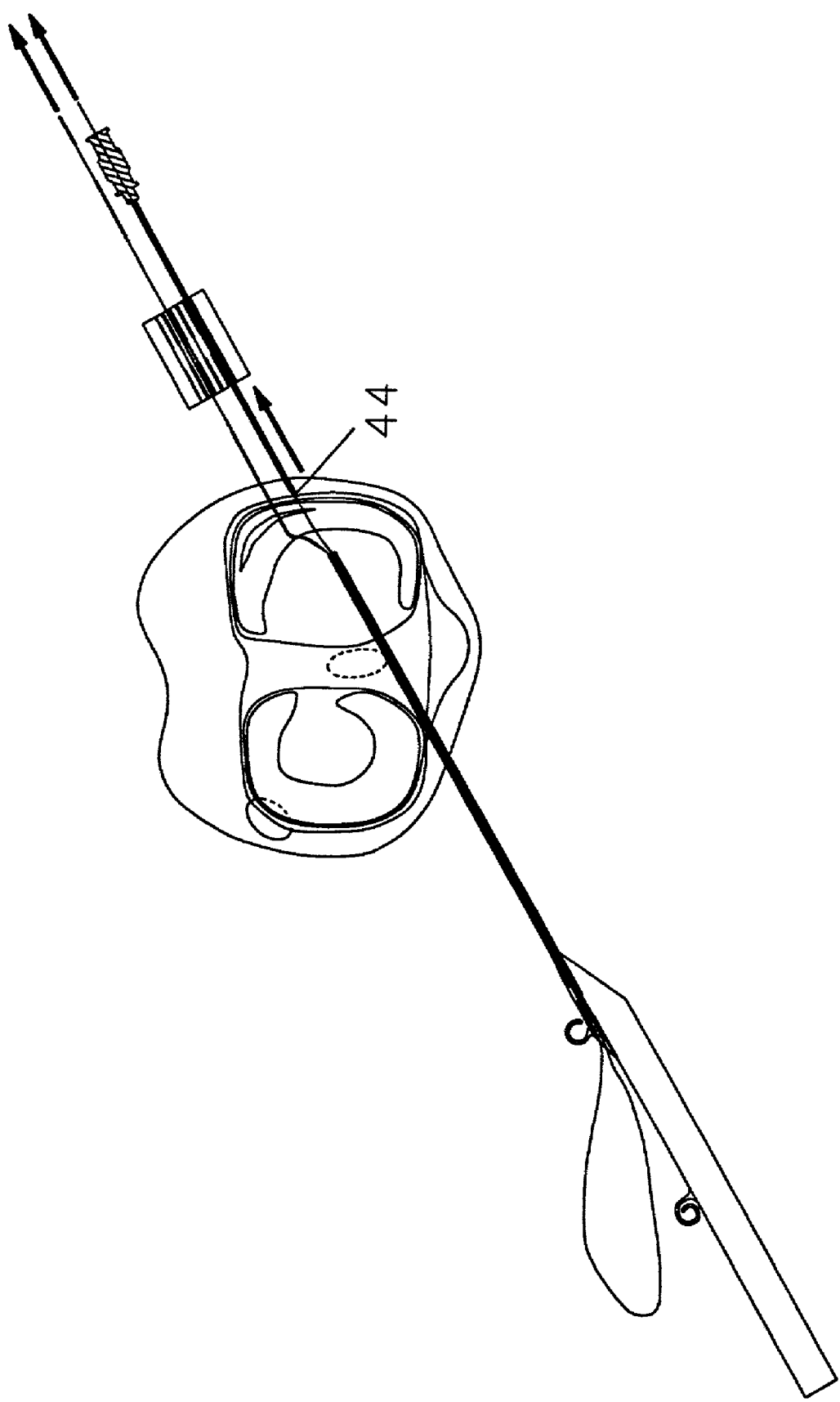

The first needle is removed, and with the two limbs of the suture held separately by the proximal and distal loops, one limb of the suture is advanced by sliding the suture with the index finger over the top surface of the handle so that the suture emerges from the tip of the cannula (FIG. 20). The suture, via the suture passer, is now fully controllable with one hand. The tip of the second needle and the tip of the cannula are brought into close proximity and the suture is passed from the loaded suture passer into the opening of the second needle and through the second needle. The suture is advanced until it exits from the hub of the second needle (FIG. 21). The second needle is partially removed so that the tip of the second needle is buried within soft tissue 44 (FIG. 22). The suture is disengaged from the guides on the handle of the suture passer.

Figure 23:
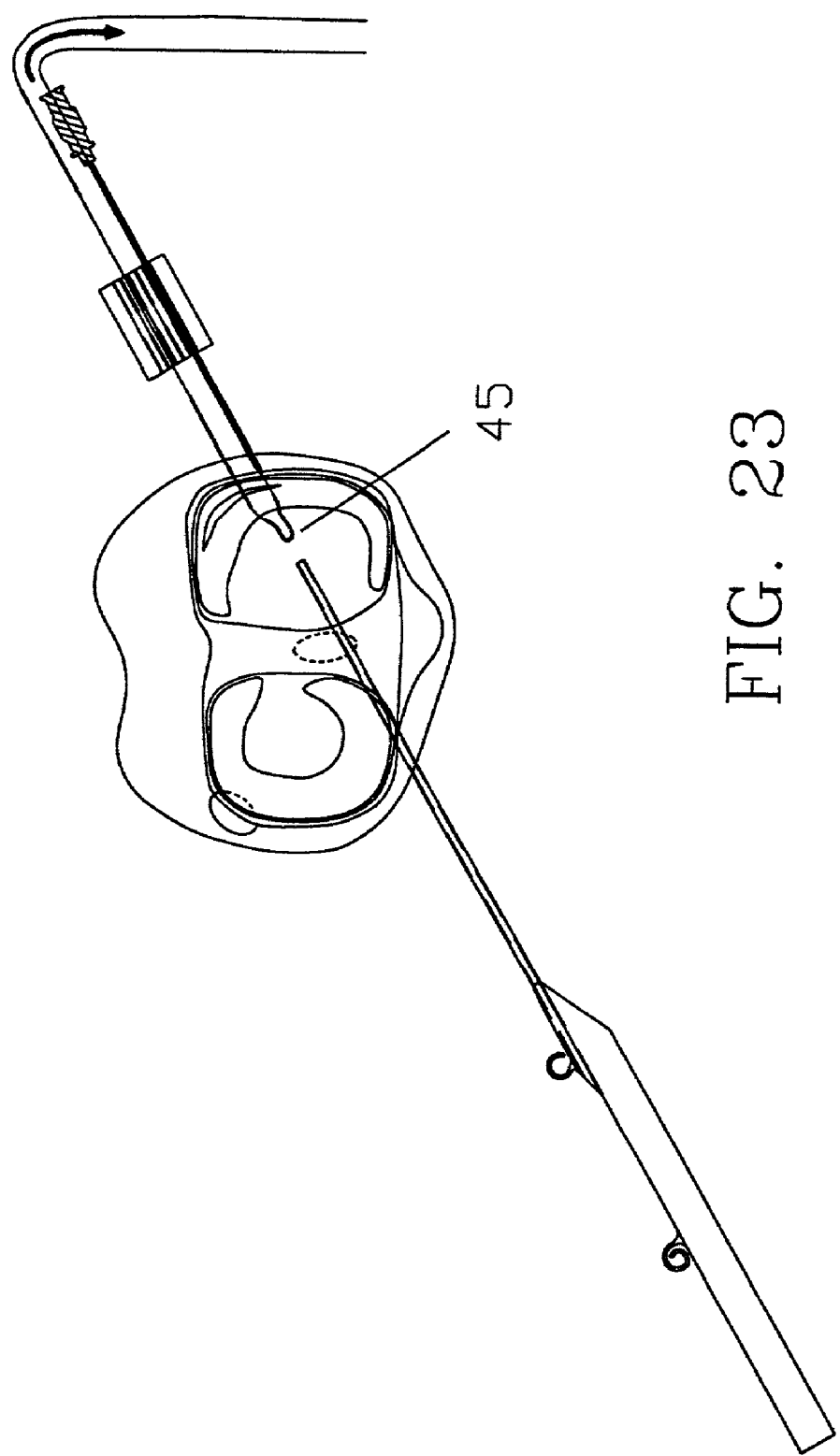
Figure 24:
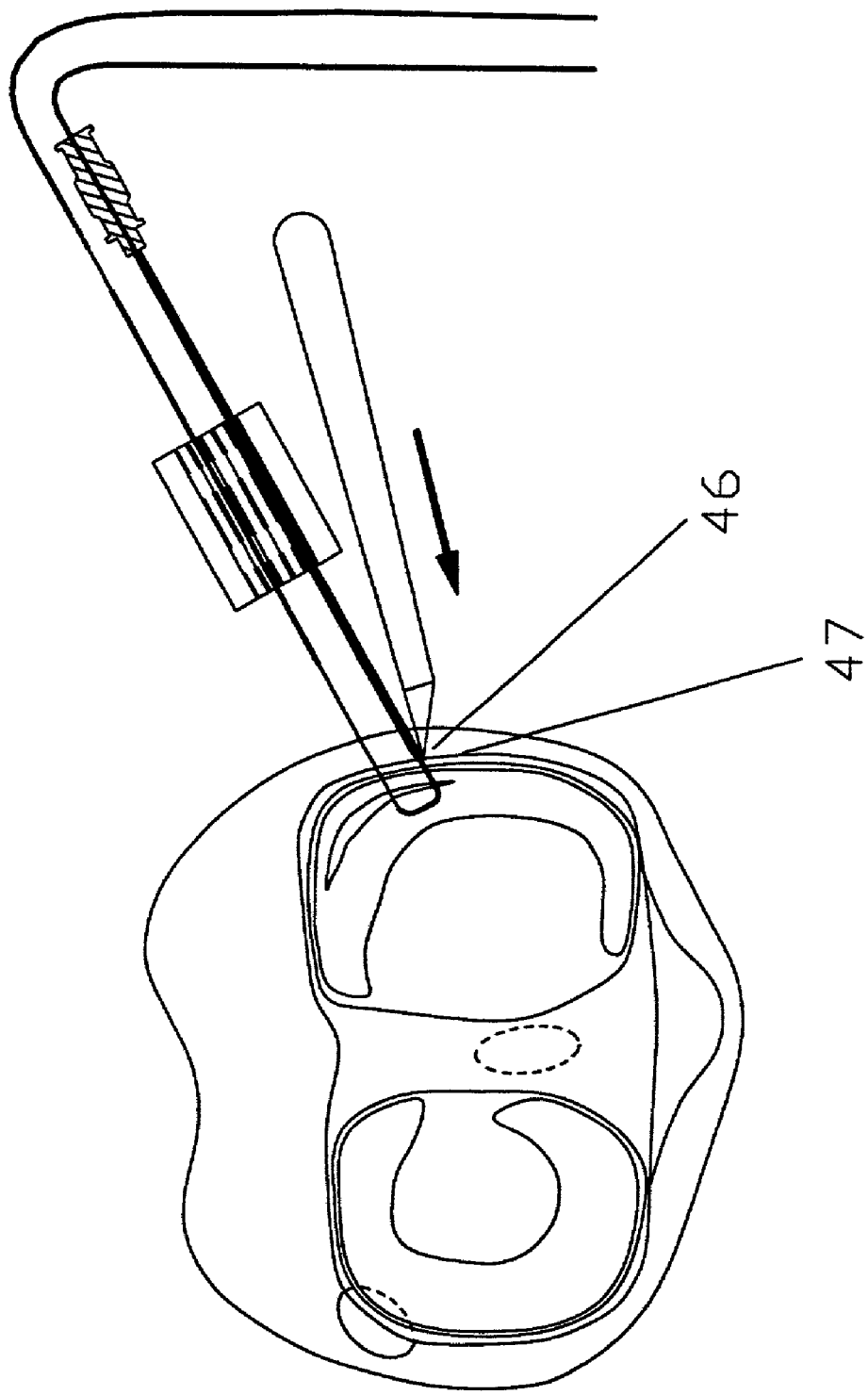
Figure 25:
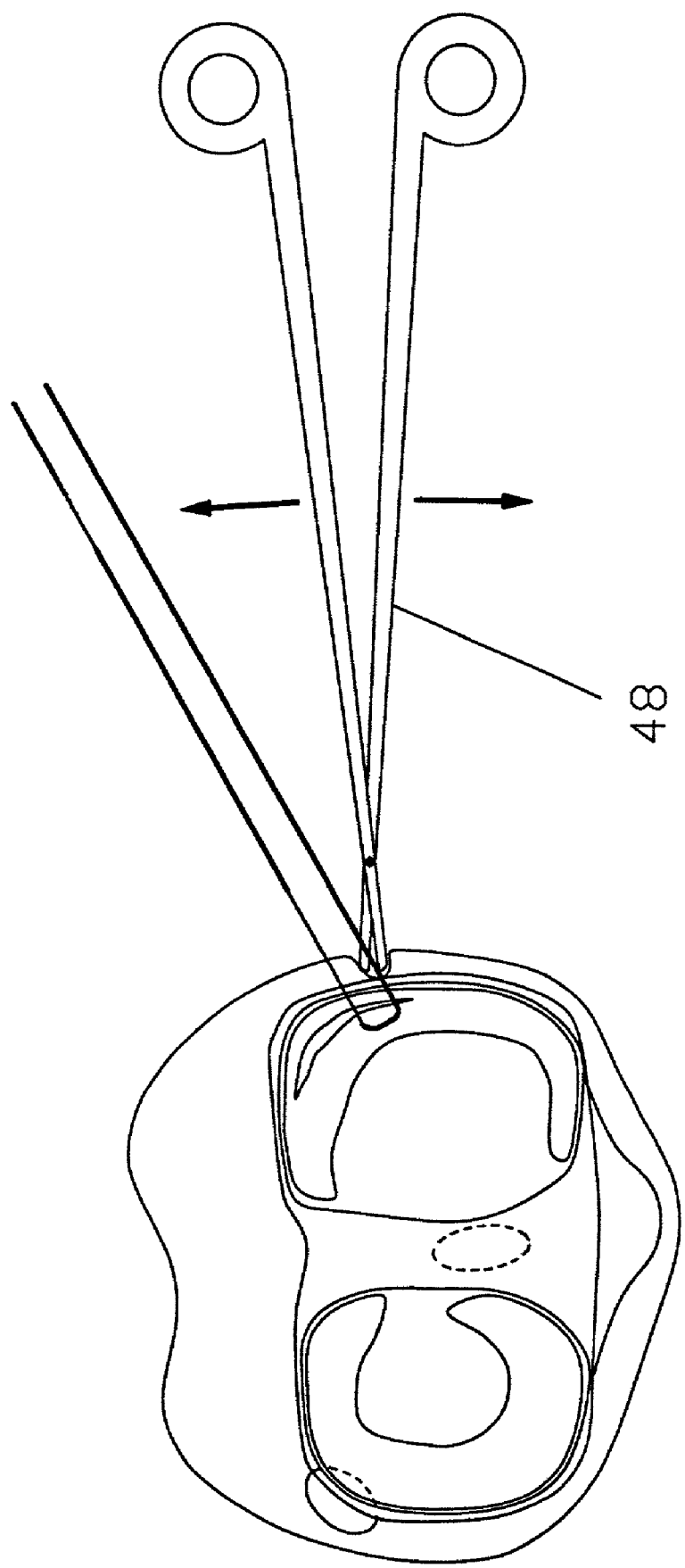
Figure 26:
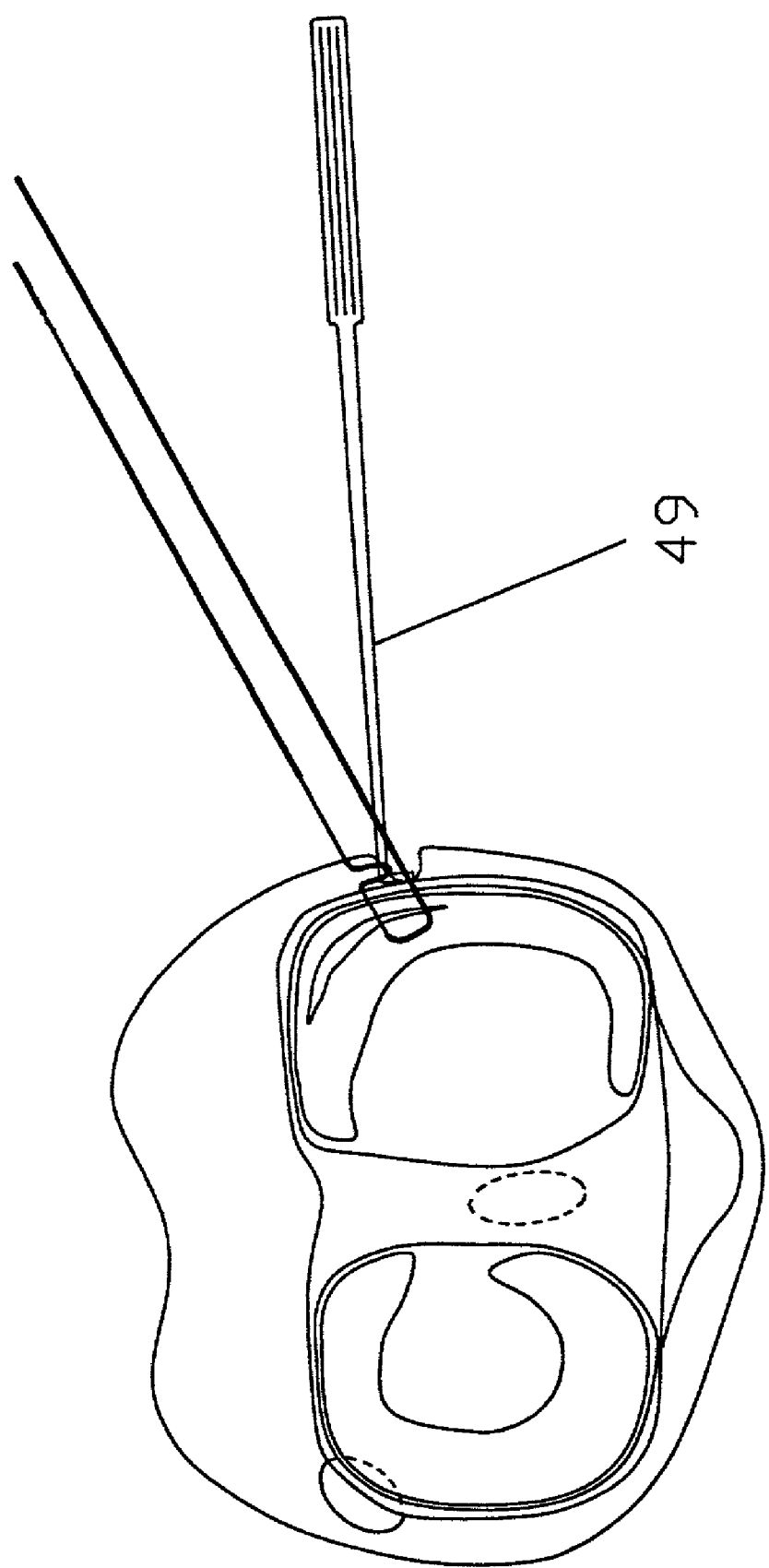

While grabbing both ends of the suture, the suture is pulled through the cannula into a joint 45 (FIG. 23). With the second needle still in place, a stab incision is made along the shaft of the second needle down to the level of a joint capsule 47 but not beyond (FIG. 24). The second needle is removed and the soft tissue is dissected all the way down to the joint capsule by spreading the soft tissue with a pair of small forceps 48 (FIG. 25). The other limb of the suture is then retrieved through this "stab incision" with a meniscal probe 49 (FIG. 26) and the sutures are tied after all of the sutures have been put into place.

Figure 27A:
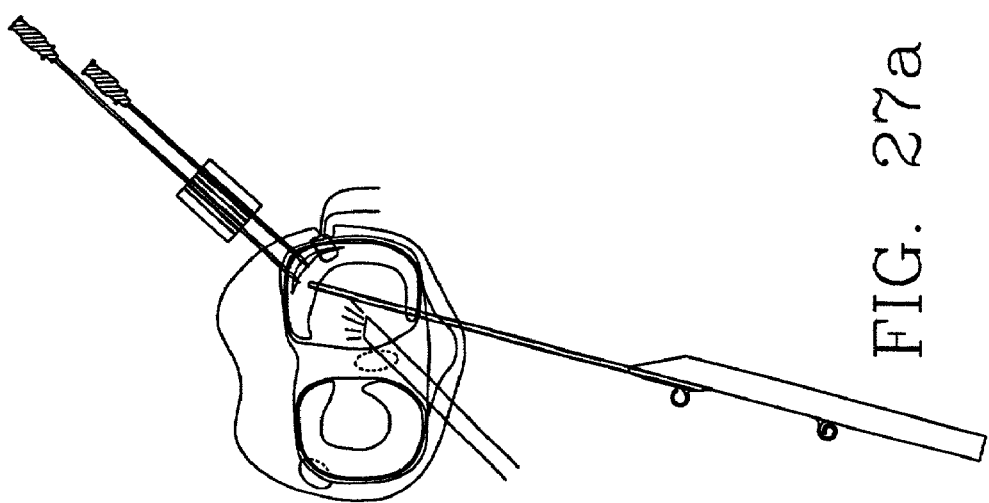
FIG. 27A, FIG. 27B, and FIGS. 28–31 are cross-sectional top views at various stages of an operation where the posterior region of the meniscus is being repaired.
Figure 27B:
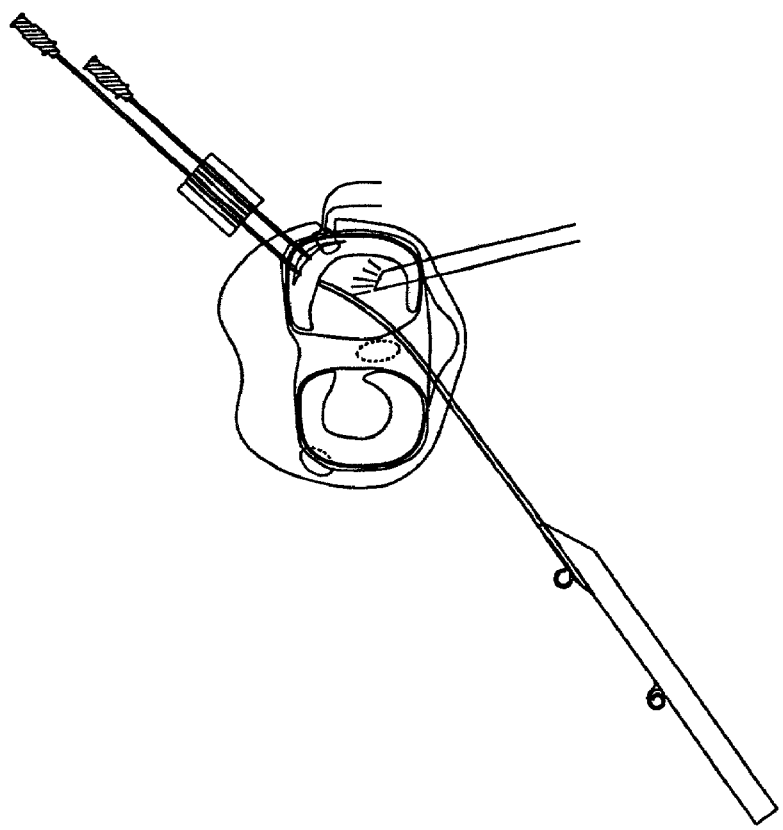

For a meniscal tear in the more posterior position, the straight cannula can enter through the ipsilateral portal to reach the posterior horn of the meniscus (FIG. 27a). The cannula can also be contoured to reach a specific zone of the meniscus with the use of the cannula bender and the template for the various zones (FIG. 27b).

Figure 28:
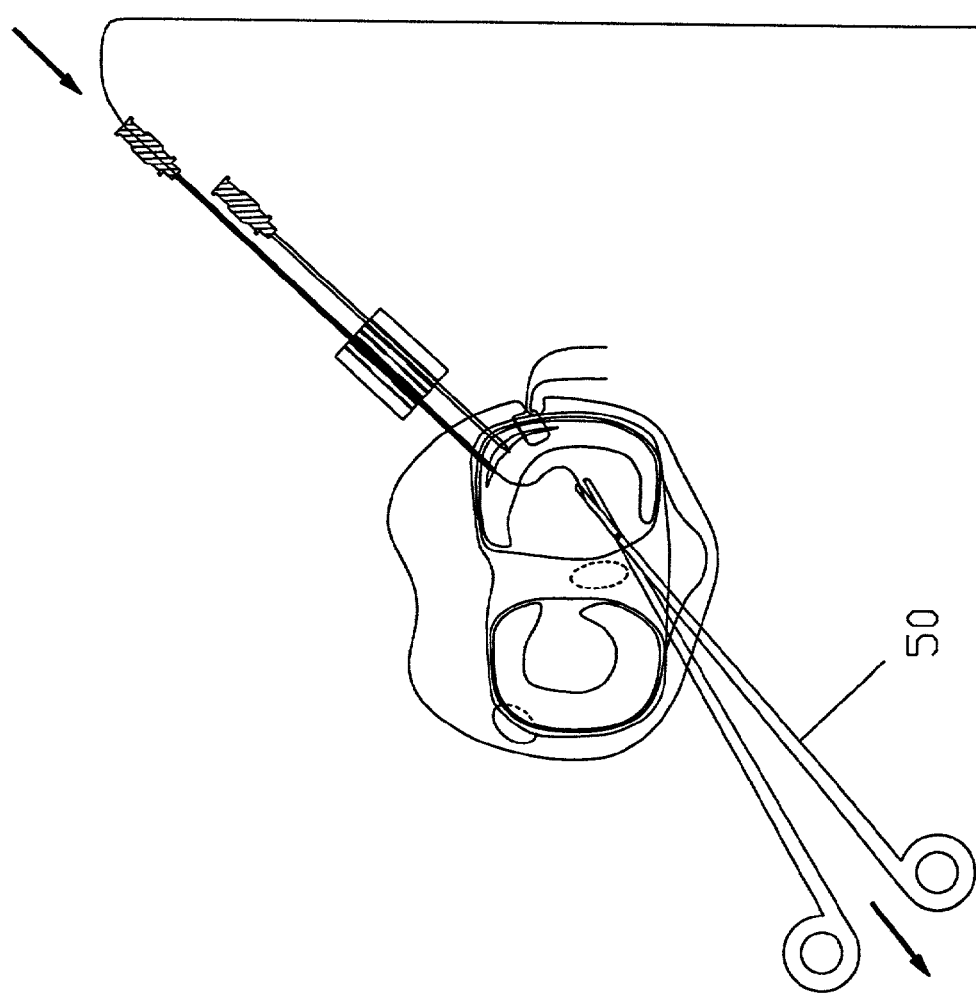
Figure 29:
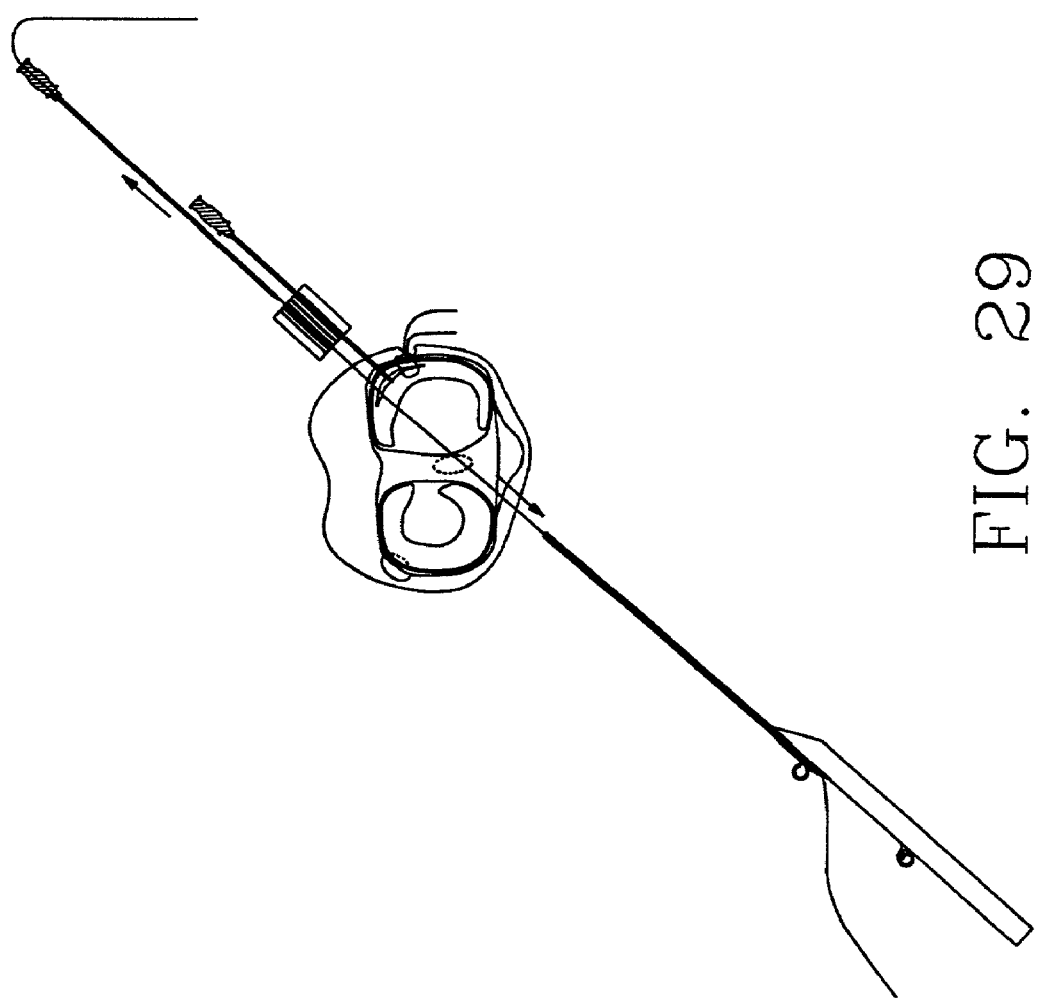
Figure 30:
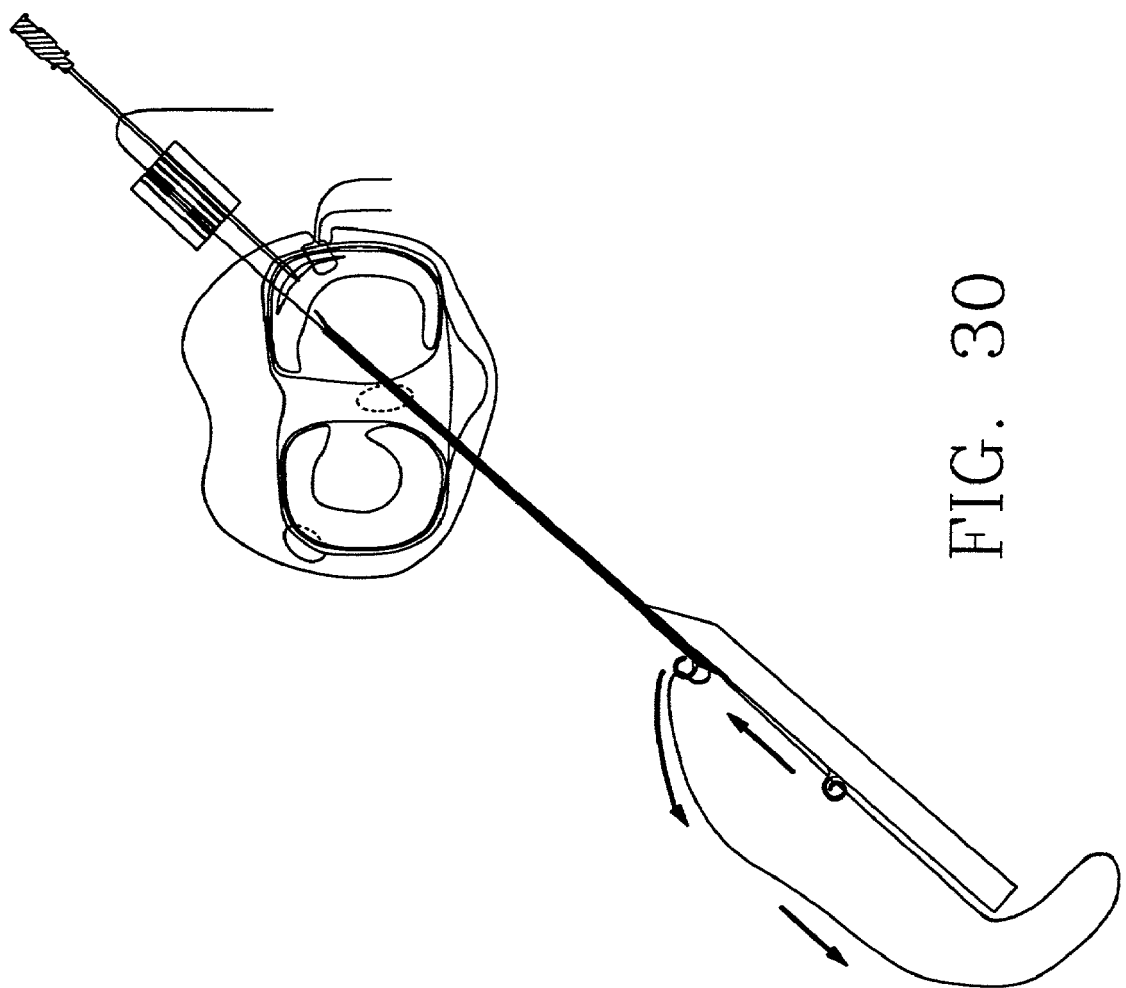

During repair of the meniscus, if the tip of the cannula cannot engage the tip of the needle during initial passage of the suture, the suture may be fed through the posterior needle into the joint. The suture may then be retrieved with a snap or a suture retriever 50 (FIG. 28). The first needle is removed and the suture is fed into the cannula in a retrograde direction (FIG. 29). The cannula is advanced into the joint along the suture. The suture is then looped onto the distal guide and threaded back into the cannula until it reaches the tip of the cannula. The suture is then engaged onto the proximal guide (FIG. 30).

Figure 31:
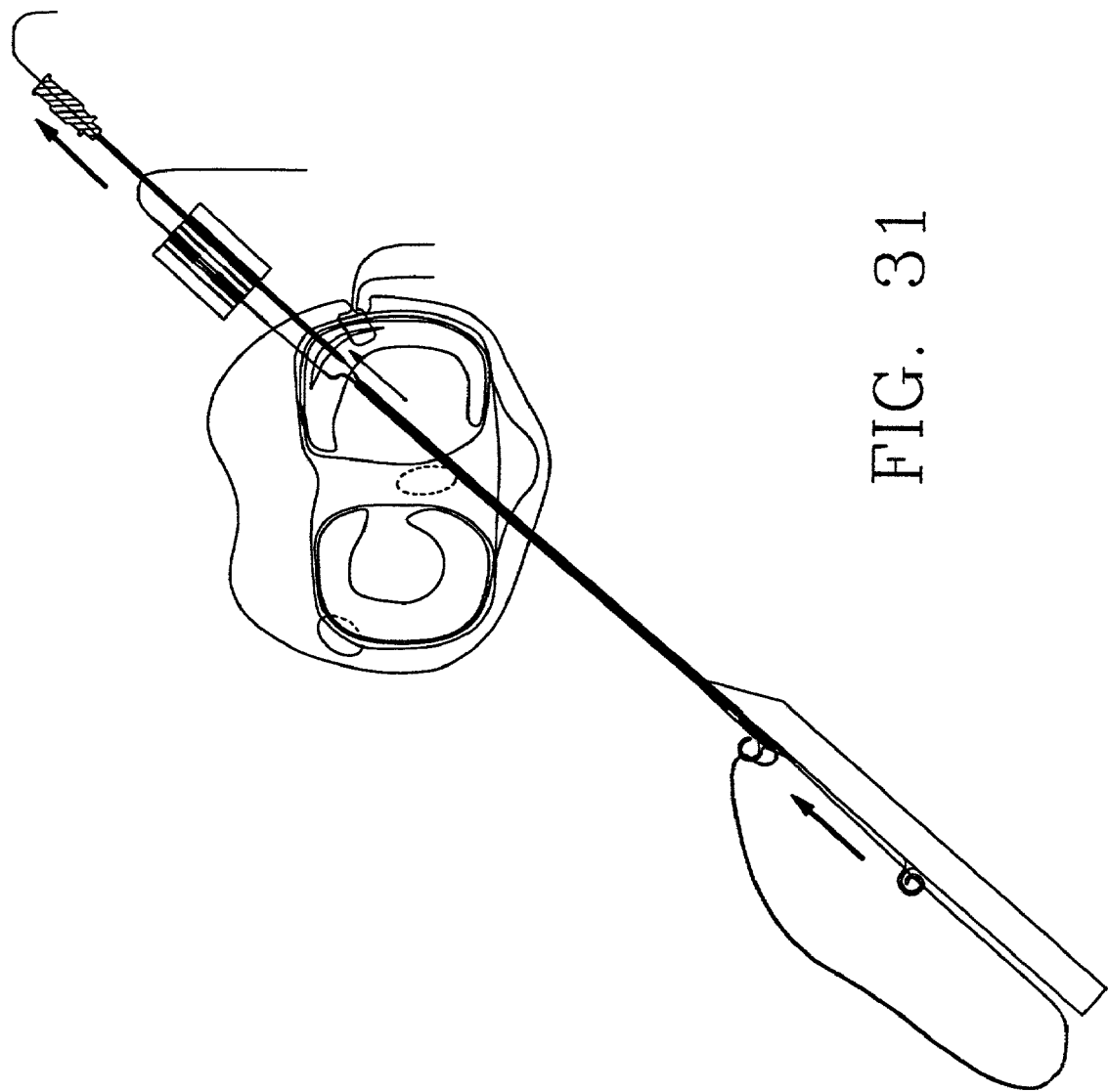
Figure 34:
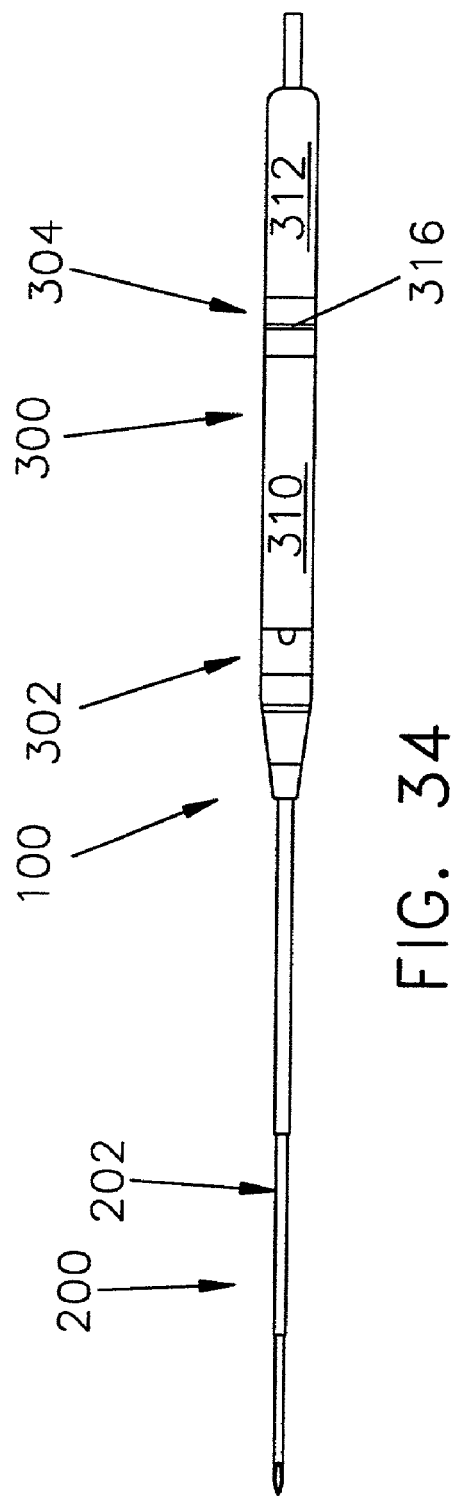
FIG. 34 is a top view of the modular suture passer shown in FIG. 32.
Figure 35:
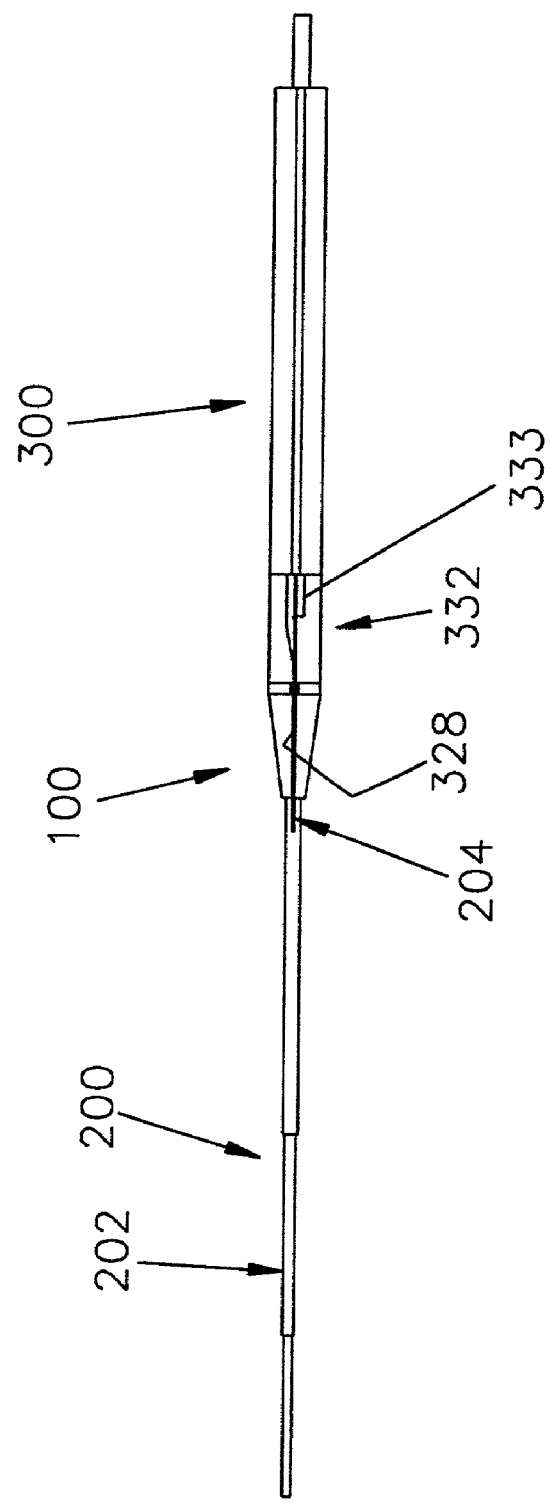
FIG. 35 is a bottom view, with portions broken away, of the modular suture passer shown in FIG. 32.
Figure 37A:
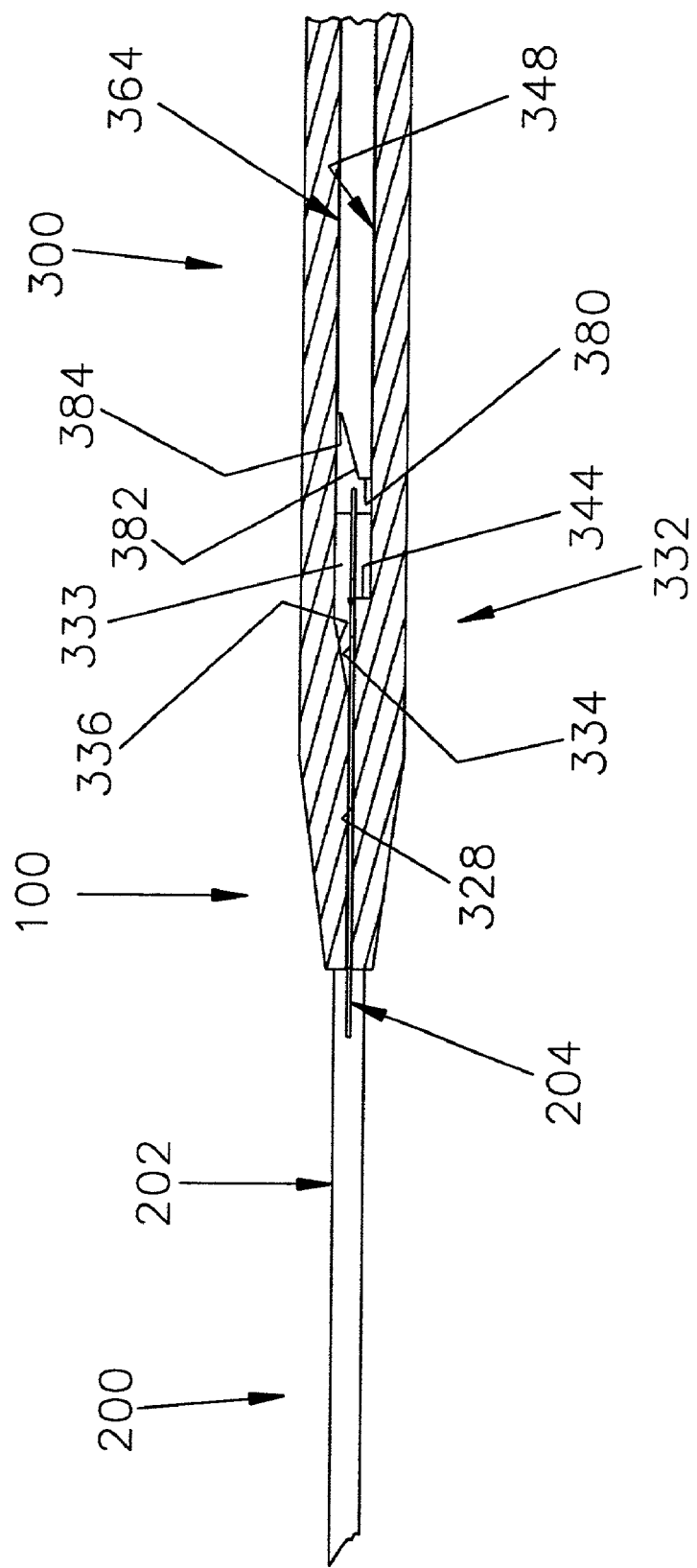
FIG. 37A is an enlarged bottom view showing selected portions of FIG. 37 in greater detail.
Figure 39A:
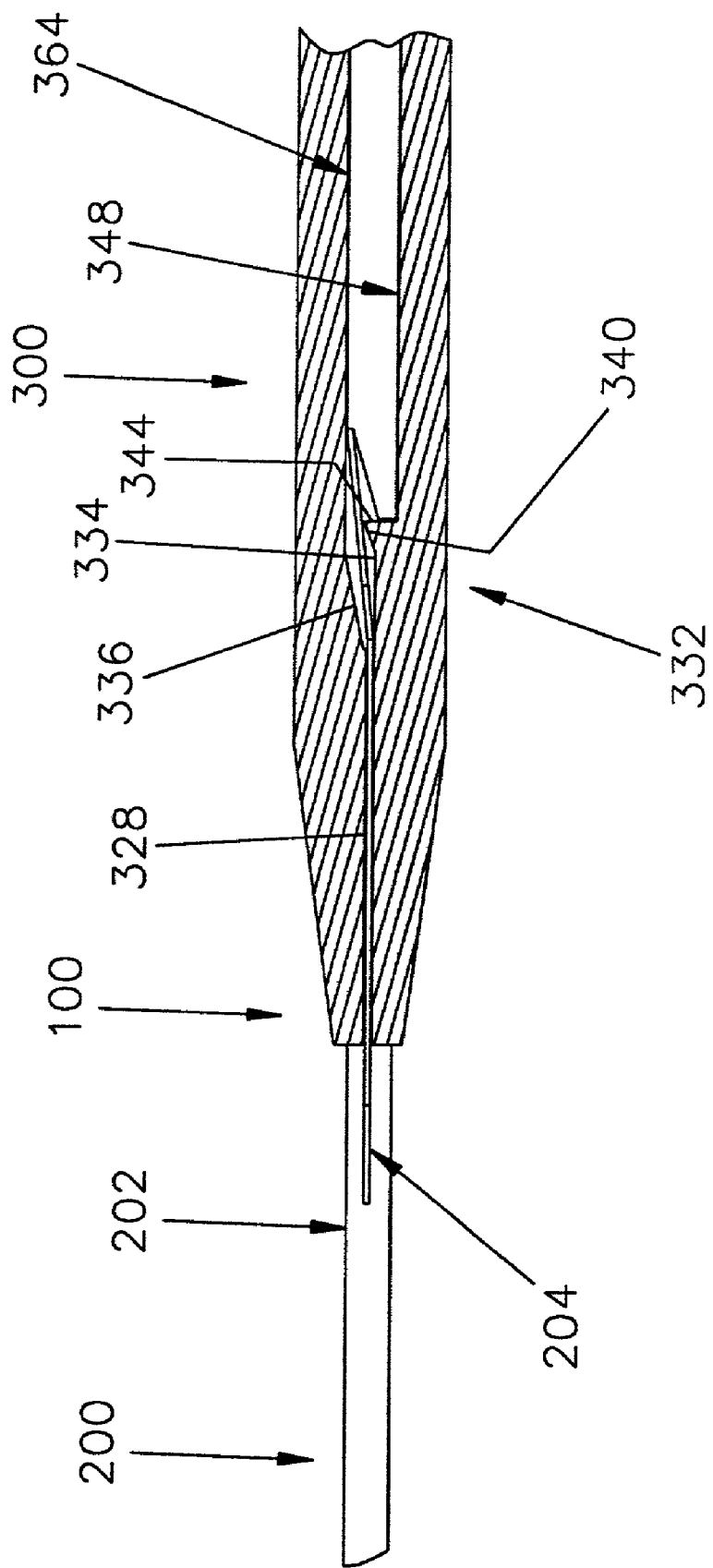
FIG. 39A is an enlarged bottom view showing selected portions of FIG. 39 in greater detail.
Figure 46:
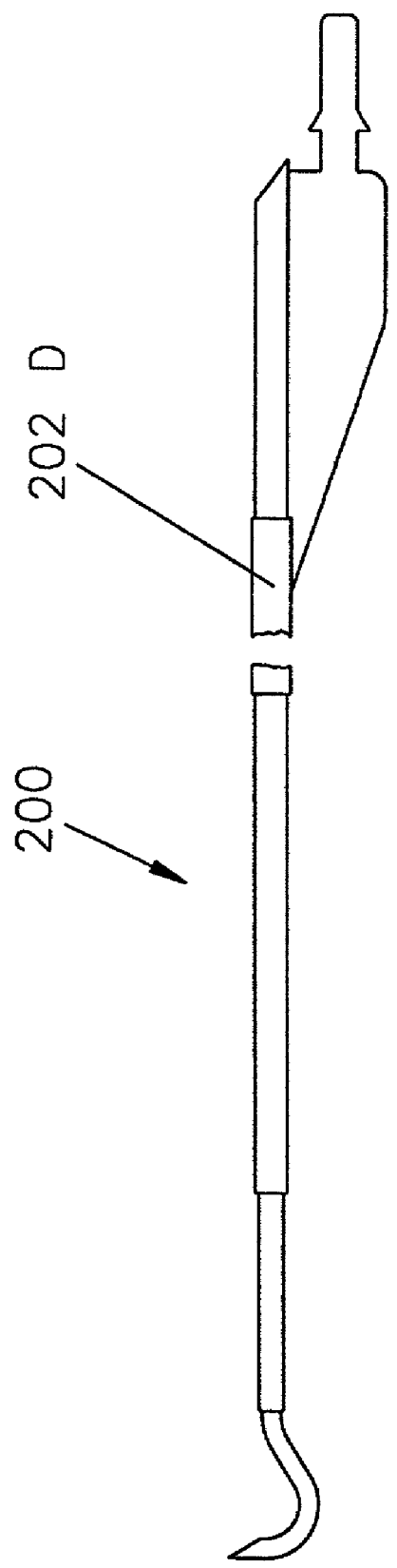
FIG. 46 is an enlarged left side view, partially cut away, of yet another cannula suitable for use with the modular suture passer shown in FIGS. 32–39.
Figure 47:
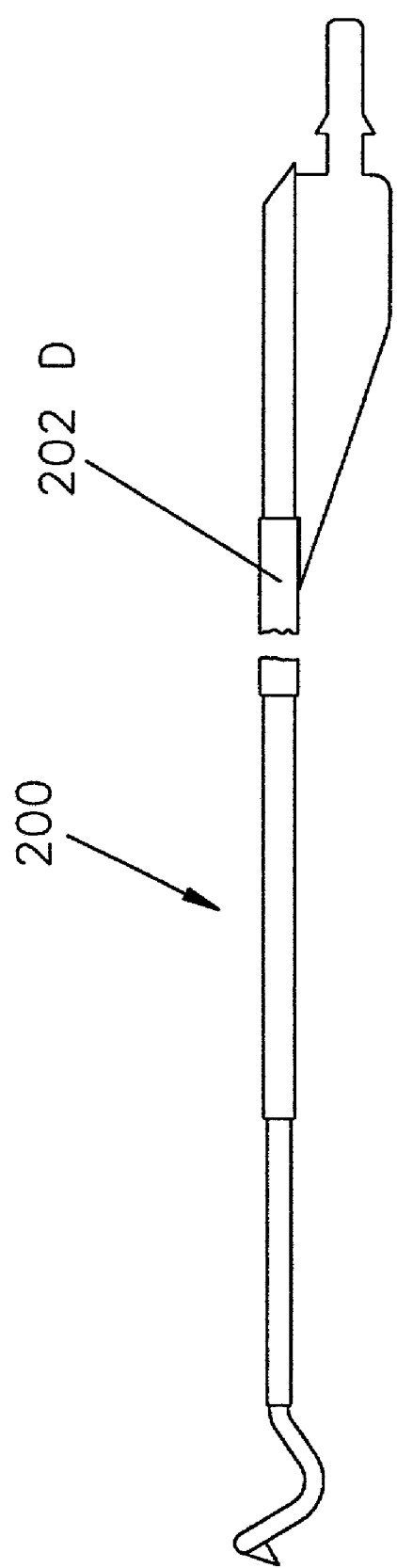
FIG. 47 is an enlarged left side view, partially cut away, of still another cannula suitable for use with the modular suture passer shown in FIGS. 32–39.

The suture is then advanced into the tip of the second needle under arthroscopic visualization (FIG. 31). The suture is advanced until it exits from the hub of the second needle. The second needle is slightly pulled back so that the tip of the needle is buried within the soft tissue. The suture is disengaged from the guides on the handle of the suture passer and the suture is pulled through the cannula into the joint.

The suture passer can also be used to pass the suture from the suture passer to the hollow needles, instead of vice versa. The suture passer is loaded with a suture so that the suture engages the first and second guide means with the "beginning" and "terminal" ends of the suture protruding from the distal opening of the hollow cannula. The beginning end of the suture is fed from the distal opening of the hollow cannula through the opening of the first hollow needle until it exits the first hollow needle. The terminal end of the suture is passed from the distal opening of the hollow cannula through the opening of the second hollow needle until it exits the second hollow needle. The suture is then completely disengaged from the suture passer, the suture passer is removed, both hollow needles removed and the suture is tightened and tied.

By maneuvering the tip of the needle with one hand and the cannula in the other when both tips are in close proximity, the suture may be advanced.

In another method, the suture protrudes from the cannula by about ½ to 1 centimeter. By manipulating the tip of the cannula with the tip of the needle, one can engage the suture into the tip of the needle and advance the suture.

An arthroscopic video camera may be used to visualize the suturing. The surgeon manipulates the suture preferably while viewing a video monitor connected to the camera.

A recommended suture for use is the Ethicon "O" PDS suture. The length of the suture should be at least 27 inches and preferably 36 inches in length. With other types of monofilament suture, the strand tends to be curled when removed from the packaging. It is necessary to straighten out the suture prior to use, as the ends of the suture must be straight for ease of passage of the suture between the cannula and the needle.

It is preferable that the suture being used have distinct markings to give an enhanced visual indication of the movement of the suture. Different types and colors or markings along the length of the suture will indicate how much suture has been advanced. It is preferred that the suture have distinct markings at the beginning and terminal ends of the suture, which could indicate the length of the suture which has been advanced.

If the meniscal tear is large, the repair operation should begin at the anterior portion of the tear. After the placement of the anterior suture, it will be easier to work along the anterior joint line to the posterior part of the tear. The medial meniscus is repaired with the knee in near extension or slight flexion. The lateral meniscus is repaired with the knee in 45° to 90° flexion.

In a further modification of the invention, the suture passer may be formed in a modular fashion so that a variety of different cannulas can be attached to its handle. These cannulas may be blunt (in the manner shown in FIGS. 1–3, 6, 7A, 7B, 14–23, 27A, 27B and 29–31) or sharply pointed, and they may be pre-formed straight (in the manner shown in FIGS. 1–3, 6, 7A, 7B, 14–23, 27A and 29–31) or already curved.

More particularly, and looking now at FIGS. 32–43, a modular suture passer 100 is shown. Suture passer 100 generally comprises a cannula 200 and a handle 300. Cannula 200 and handle 300 are configured for releasable locked engagement with one another.

More particularly, and still looking now at FIGS. 32–43, cannula 200 comprises an elongate tubular member 202 and a thin, outwardly extending radial fin 204. Fin 204 is attached to tubular member 202 adjacent to the tubular member's proximal end 206 (see FIGS. 36, 38 and 40).

Tubular member 202 may be formed out of a single piece of tubing if desired. Alternatively, it may be formed out of a plurality of concentric tubes so as to increase the rigidity of tubular member 202, e.g. to assist in penetrating tough tissue. In the specific embodiment shown in FIGS. 32–43, tubular member 202 is shown formed out of three concentric tubes 202A, 202B and 202C (see FIGS. 40 and 42). The inner diameter of tube 202C is selected so as to engage the outer diameter of tube 202B, and the inner diameter of tube 202B is selected so as to engage the outer diameter of tube 202A. In addition, tube 202A is sized so as to have the longest length, tube 202C is sized so as to have the shortest length, and tube 202B is sized so as to have an intermediate length. The proximal ends of tubes 202A, 202B and 202C are aligned with one another so that tube 202B projects out of tube 202C and tube 202A projects out of tube 202B, and then the resulting structure is secured in place by welding or some other suitable process. It will be appreciated that a cannula 200 comprising the foregoing structure will be quite strong.

The cannula's fin 204 comprises a main portion 208 and a tab portion 210 (see FIGS. 36, 38, 40 and 41).

Main portion 208 has a proximal edge 212 (see FIG. 40) which is substantially aligned with the proximal end 206 of the cannula's tubular member 202. Main portion 208 also has a bottom edge 214 which is spaced from the outer surface of tubular member 202 by a distance which is slightly less than the height of handle 300 (see FIG. 36). Main portion 208 also has a distal edge 216 (see FIG. 40) which extends between the main portion's bottom edge 214 and the outer surface of tubular member 202.

Tab portion 210 extends centrally and proximally from proximal edge 212 of the fin's main portion 208 (see FIG. 40). Tab portion 210 is located in the same plane as main portion 208 (see FIG. 41) and is preferably generally rectangular in shape, although other tab shapes may also be used without departure from the present invention. Tab portion 210 includes an upper tab projection 218 (see FIG. 40) which projects upwardly out of the tab portion's upper edge 220, and a lower tab projection 222 which projects downwardly out of the tab portion's lower edge 224. Upper tab projection 218 defines an upper, distally facing tab shoulder 226, and lower tab projection 222 defines a lower, distally facing tab shoulder 230. Tab projections 218 and 222 are located between the proximal edge 212 of the fin's main portion 208 and the proximal edge 232 of tab portion 210 (see FIG. 40). Tab shoulders 226 and 230 are aligned with one another.

Looking next at FIGS. 32–39 and 39A, handle 300 comprises a first suture guide 302 and a second suture guide 304.

First suture guide 302 includes an eyelet 306 (see FIGS. 32 and 33). A passageway 308 is provided to permit a length of suture (not shown in FIGS. 32–39 and 39A) to be slid transversely into eyelet 306.

Still looking now at FIGS. 32–39 and 39A, second suture guide 304 comprises a generally semi-cylindrical member extending upwardly out of the handle's top side, between the handle's distal upper surface 310 (see FIGS. 32–34) and its proximal upper surface 312. An axial bore 314 (see FIGS. 36 and 38) extends longitudinally through second suture guide 304. A top slot 316 (see FIGS. 32–34 and 36) extends down into second suture guide 304, transverse to the longitudinal axis of the handle. A right side slot 318 (see FIGS. 33 and 36) extends between the second suture guide's distal end 320 and its top slot 316. A left side slot 322 (see FIG. 32) extends between the second suture guide's proximal end 324 and its top slot 316. Top slot 316, right side slot 318 and left side slot 322 effectively bifurcate second suture guide 304 into a pair of closely spaced, oppositely extending fingers. These fingers can be considered to be somewhat analagous to the fingers 14–16 shown in FIGS. 7A and 7B and described above. In view of the foregoing construction, a length of suture (not shown in FIGS. 32–39 and 39A) may be aligned parallel to the second suture guide's top slot 316, then dropped into the top slot, and thereafter rotated 90° into the right side slot 318 and 90° into the left side slot 322, so that the suture enters the interior bore 314 of second suture guide 304.

Still looking now at FIGS. 32–39 and 39A, handle 300 also comprises a first bore 326 (see FIGS. 36 and 38) which extends proximally and axially from the distal end of the handle toward the proximal end of the handle. First bore 326 includes a stop 327 (see FIGS. 36 and 38) at its proximal end. First bore 326 is sized so as to be able to receive the proximal portion of a cannula's tubular member 202. First bore 326 is positioned so that when the cannula's tubular member 202 is received in the handle's first bore 326, the central lumen of the tubular member will open onto the handle's distal upper surface 310, between first suture guide 302 and second suture guide 304 (see FIG. 36).

A vertical slot 328 (see FIGS. 35–37, 37A, 38, 39 and 39A) extends downwardly from first bore 326. Vertical slot 328 opens on the handle's bottom surface 330 (see FIG. 36), and is sized to receive the main portion 208 of a fin 204 when a cannula 200 is mounted to handle 300.

Still looking now at FIGS. 32–39 and 39A, a snap lock 332 (see FIGS. 35–37, 37A, 38, 39 and 39A) is formed at the proximal end of vertical slot 328. Snap lock 332 comprises a cavity 333 formed in handle 300 immediately proximal to slot 328 (see FIGS. 35–37, 37A and 38). Cavity 333 is sized to receive the tab portion 210 of a fin 204 when a cannula 200 is mounted to handle 300. The right sidewall of cavity 333 comprises a proximally extending continuation 334 (see FIGS. 37A and 39A) of the right sidewall of vertical slot 328. Continuation 334 has a length substantially equal to the distance between the proximal edge 212 of the cannula's main fin portion 208 and the distally facing tab shoulders 226 and 230 of the cannula's tab portion 210 (see FIG. 40). The left sidewall of cavity 333 comprises an outward tapering 336 (see FIGS. 37A and 39A) of the left sidewall of vertical slot 328.

Snap lock 332 also comprises a sloping upper sidewall projection 338 (see FIGS. 36 and 38) extending inwardly into cavity 333 from the continuation 334 of the right sidewall of vertical slot 328, and a sloping lower sidewall projection 340 (see FIGS. 37, 38 and 39A) extending inwardly into cavity 333 from the same continuation 334. Upper sidewall projection 338 defines an upper, proximally facing sidewall shoulder 342 (see FIG. 38) and lower sidewall projection 340 defines a lower, proximally facing sidewall shoulder 344 (see FIGS. 37A, 38 and 39A). Upper sidewall shoulder 342 is aligned with lower sidewall shoulder 344.

Upper and lower sidewall projections 338 and 340 are located such that as the tab portion 210 of a given cannula 200 enters the handle's cavity 333, the cannula's upper and lower tab projections 218 and 222 will snap over and lockingly engage the handle's upper and lower sidewall projections 338 and 340 when the cannula is fully inserted into the handle's first bore 328. In particular, when the assembly is in this locked condition, the cannula's distally facing upper tab shoulder 226 will engage the handle's proximally facing upper sidewall shoulder 342, and the cannula's distally facing lower tab shoulder 230 will engage the handle's proximally facing lower sidewall shoulder 344 (see FIG. 36).

When a given cannula 200 has been mounted to the handle 300 in the foregoing manner, rotational movement of the cannula relative to the handle is precluded by the engagement of the cannula's main fin portion 208 with the sidewalls of the handle's slot 328. In addition, axial movement of the cannula relative to the handle is precluded (i) in the proximal direction by the engagement of the proximal end 206 of the cannula 200 with the stop 327 located at the proximal end of the handlers first bore 326, and (ii) in the distal direction by the engagement of the cannula's two distally facing tab shoulders 226 and 230 with the handle's two proximally facing sidewall shoulders 342 and 344.

The handle of the modular suture passer 100 also includes means for releasing a cannula from its locking engagement with the handle. More particulary, and still looking now at FIGS. 32–39 and 39A, a second longitudinal bore 348 (see FIGS. 36, 37, 37A, 38, 39 and 39A) extends between the proximal end 350 (see FIG. 36) of cavity 333 to the proximal end 352 (see FIGS. 36 and 38) of handle 300. Second bore 348 includes a distal portion 354 (see FIGS. 36 and 38) communicating with cavity 333, an enlarged intermediate portion 356, and a proximal portion 358 opening on the handle's proximal end 352. A proximally facing annular shoulder 360 (see FIGS. 36 and 38) is formed at the intersection of the bore's distal portion 354 with its intermediate portion 356, and a distally facing annular shoulder 362 is formed at the intersection of the bore's proximal portion 358 with its intermediate portion 356. The bore's distal portion 354 is sized so that the proximalmost portion of cannula tab 210 may be contained therein (see FIG. 36).

A release rod 364 (see FIGS. 36, 37, 37A, 38, 39 and 39A) is slidably disposed in second bore 348. More particularly, release rod 364 comprises a distal portion 366 (see FIGS. 36 and 38), an enlarged intermediate portion 368, and a proximal portion 370. A distally facing annular shoulder 372 (see FIGS. 36 and 38) is formed at the intersection of the rod's distal portion 366 and its intermediate portion 368, and a proximally facing annular shoulder 374 is formed at the intersection of the rod's proximal portion 370 and its intermediate portion 368. A spring 376 (see FIGS. 36 and 38) is captivated between bore shoulder 360 and rod shoulder 372 so as to bias release rod 364 proximally (see FIGS. 36 and 37). The engagement of rod shoulder 374 with bore shoulder 362 limits proximal movement of release rod 364. Release rod 364 can be urged distally against the power of spring 376 by pressing on the rod's proximal end 378 (see FIGS. 38 and 39). The distal end of release rod 364 is bevelled so as to form an end surface 380, a deflection surface 382, and a drive surface 384 (see FIG. 37A).

To release a cannula 200 from handle 300, the proximal end 378 (see FIGS. 36 and 37) of release rod 364 is forced distally so as to move the release rod against the biasing force of spring 376. As release rod 364 moves distally through handle bore 348, the release rod's deflection surface 382 (see FIG. 37A) will engage the proximal edge 232 (see FIG. 40) of the cannula's tab portion 210 and deflect the tab portion 210 laterally so as to disengage the cannula's distally facing tab shoulders 226 and 230 (see FIG. 40) from the housing's proximally facing sidewall shoulders 342 and 344 (see FIGS. 36 and 38). As release rod 364 continues to move distally through handle bore 348, the release rod's drive surface 384 (see FIG. 37A) will engage the cannula's proximal edge 232 (see FIG. 40), whereby the entire cannula will be driven distally so that the cannula's two tab projections 218 and 222 will clear the housing's two sidewall projections 338 and 340 (see FIGS. 38, 39 and 39A). This will unlock the cannula from the handle. Cannula 200 may thereafter be manually withdrawn from the handle by pulling the cannula in a distal direction.

Thus, it will be seen that a variety of different cannulas 200 can be releasably attached to the handle 300. These cannulas can be a blunt or sharply pointed, and they may be straight or curved, as required for a particular surgical procedure.

For example, a straight, sharply pointed cannula 200 is shown in FIGS. 32–43. Preferably, the pointed distal end of this cannula is formed by cutting the distal end of the cannula at a first, relatively sharp angle so as to form a sharp penetrating edge at 270 (see FIGS. 40, 42 and 43), and then at a second, somewhat less severe angle so as to form a shallower tapering edge at 272. The cannula is preferably blunted or rounded off at 274 (see FIGS. 42 and 43) so as to minimize the possibility of damaging a suture during a tissue piercing operation, as will hereinafter be discussed in further detail.

FIGS. 44 to 49 exemplify some of the other cannula configurations which may be utilized with handle 300. Specifically, these exemplary configurations include a curved, sharply pointed cannula 200 (FIG. 44); another curved, sharply pointed cannula 200 (FIG. 45); still another curved, sharply pointed cannula 200 (FIG. 46); a "corkscrew", sharply pointed cannula 200 (FIG. 47); a straight, blunt cannula 200 (FIG. 48); and a curved, blunt cannula 200 (FIG. 49). If desired, a reinforcing tube 202D (see FIGS. 45, 46, 47 and 49) can be added to the tubular member 202 so as to further strengthen the tube against undesirable bending during tissue penetration.

Still other possible cannula configurations will be well known to those skilled in the art.

It is anticipated that a surgeon will select a particular cannula 200 depending on the particular surgical procedure which is to be carried out. For example, if the surgical procedure of FIGS. 14–26 or the surgical procedure of FIGS. 27A, 27B and 28–31 is to be carried out, the surgeon might select the straight, blunt cannula of FIG. 48 or the straight, sharply pointed cannula of FIGS. 40–43.

It will also be appreciated that modular suture passer 100 can be used in many different ways to pass a length of suture through tissue. For example, FIGS. 50–52 illustrate one possible way in which a straight, sharply pointed cannula 200 might be used to pass suture through a piece of tissue 500.

Figure 50:
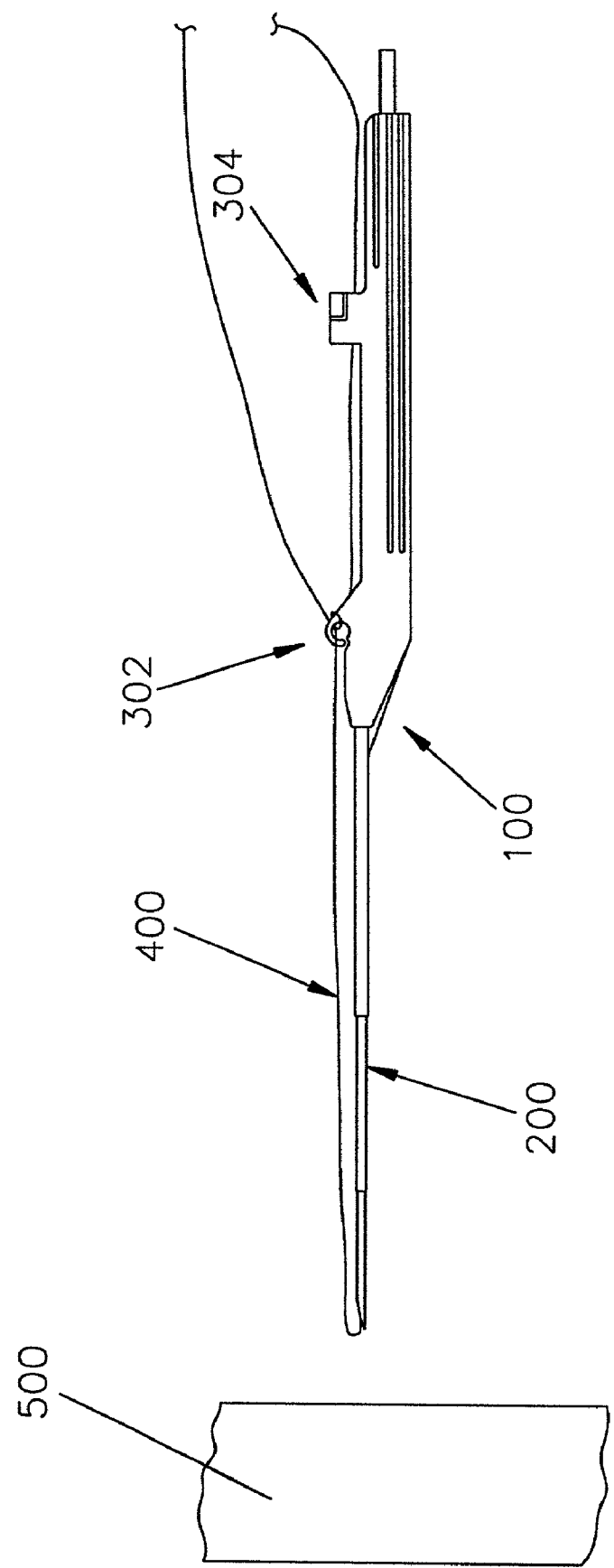
FIG. 50 is an illustrative side view showing the modular suture passer of FIGS. 32–39 adjacent to a piece of tissue, wherein a length of suture extends through the suture passer's cannula, and further wherein the suture end extending out of the distal end of the cannula engages the handle's distal suture guide, and the suture end extending out of the proximal end of the cannula engages the handle's proximal suture guide.

More particularly, and looking now at FIG. 50, a length of suture 400 may be attached to the suture passer 100 by threading the suture through the suture passer's proximal guide member 304, through its cannula 200 and then back around its distal suture guide 302. This will allow the surgeon to adequately control the two ends of the suture during the tissue penetration operation.

Figure 51:
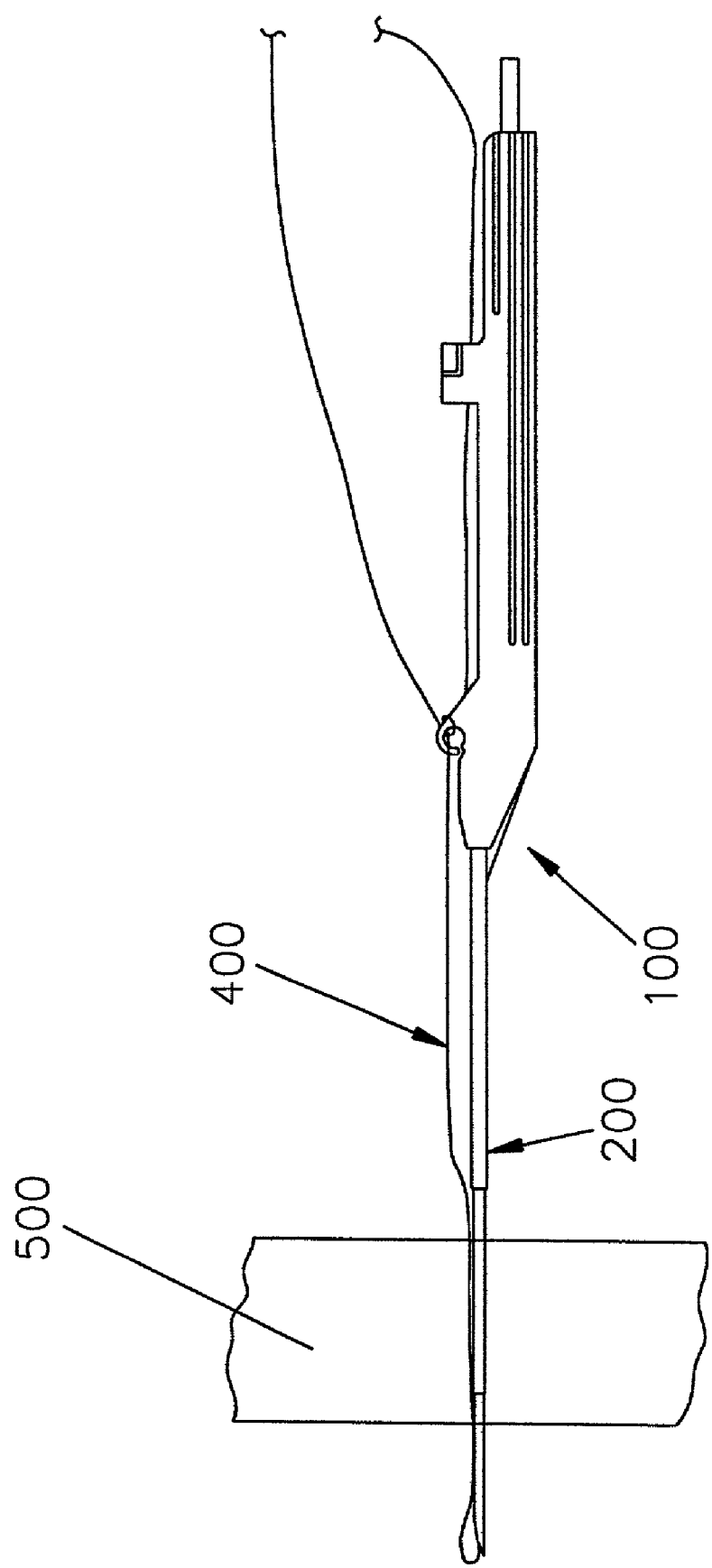
FIG. 51 is an illustrative side view similar to that of FIG. 50, except that the distal end of the cannula has been inserted through the piece of tissue, carrying the length of suture with it.
Figure 52:
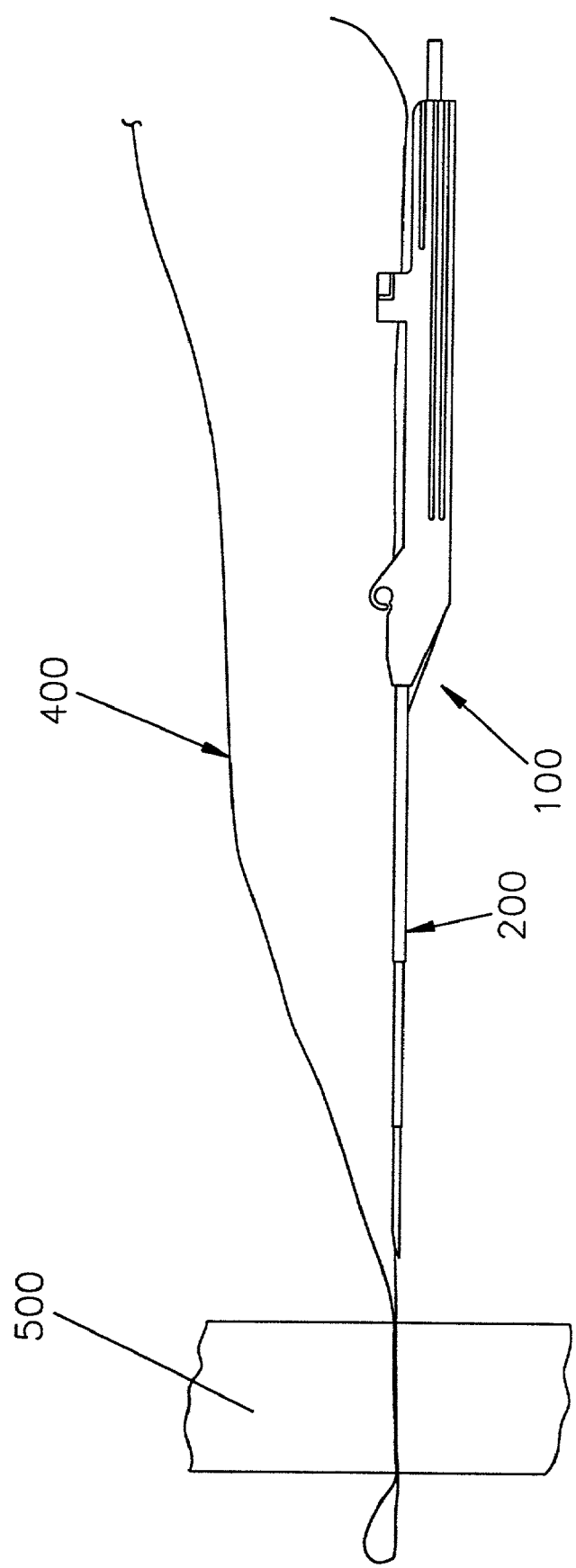
FIG. 52 is an illustrative side view similar to that of FIG. 51, except that the cannula has been withdrawn from the piece of tissue, leaving a loop of suture extending through the tissue, with the suture end extending from the distal end of the cannula having been disengaged from the handle's distal suture guide.

The pointed distal end of the suture passer's cannula 200 is then driven into and through the piece of tissue 500 (see FIG. 51). As this occurs, the suture extending out of the cannula's sharp distal tip will be forced against the blunt heel 274 (see FIG. 43) of the cannula. The cannula's blunt heel 274 will support the suture during tissue penetration and prevent the cannula from cutting or otherwise damaging the suture as the suture is carried through the tissue. Then the loop of suture residing at the far side of tissue 500 may be grasped by another tool (not shown) one or both of the suture ends freed from the suture passer 100, and suture passer 100 withdrawn from tissue 500 (see FIG. 52). At this point the suture will have been passed through tissue 500, with a loop of suture positioned on one side of the tissue and the two free suture ends positioned on the other side of the tissue.

Figures 53, 54, 55:
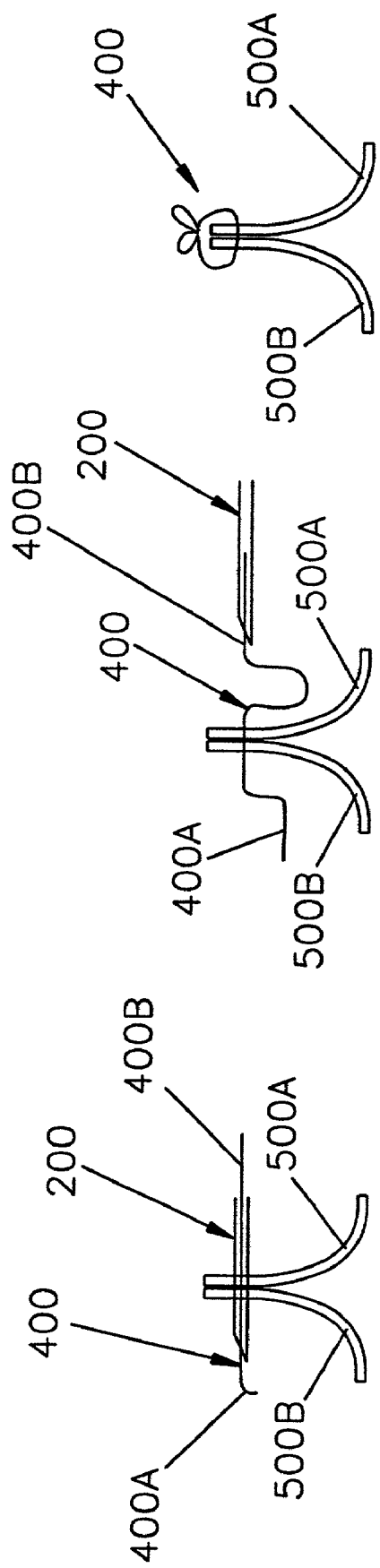
FIGS. 53–55 illustrate how a simple stitch can be established across two pieces of tissue using the present invention.

FIGS. 53–55 illustrate how a simple stitch can be established across two pieces of tissue using the present invention. More particularly, a length of suture 400 is first loaded onto suture passer 100 by feeding one end 400A of the suture into the suture passer's cannula 200. Suture end 400A is left sitting within the length of cannula 200. Suture length 400B is loaded onto the suture passer's proximal suture guide 304. The intermediate portion of suture 400 will extend along the handle's distal upper surface 310. Then the distal end of the suture passer's cannula 200 is forced through two pieces of tissue 500A and 500B until the distal end of the cannula exits the tissue. Next, the surgeon urges suture 400 distally through the cannula until suture end 400A exits the tip of the cannula (see FIG. 53). Then the suture passer is withdrawn from tissue 500A and 500B, paying out the suture as it goes, so that suture 400 extends through both pieces of tissue (see FIG. 54). Next, suture 400 is withdrawn from the suture passer and suture ends 400A and 400B are tied off into a knot (see FIG. 55).

Figures 56, 57, 58:
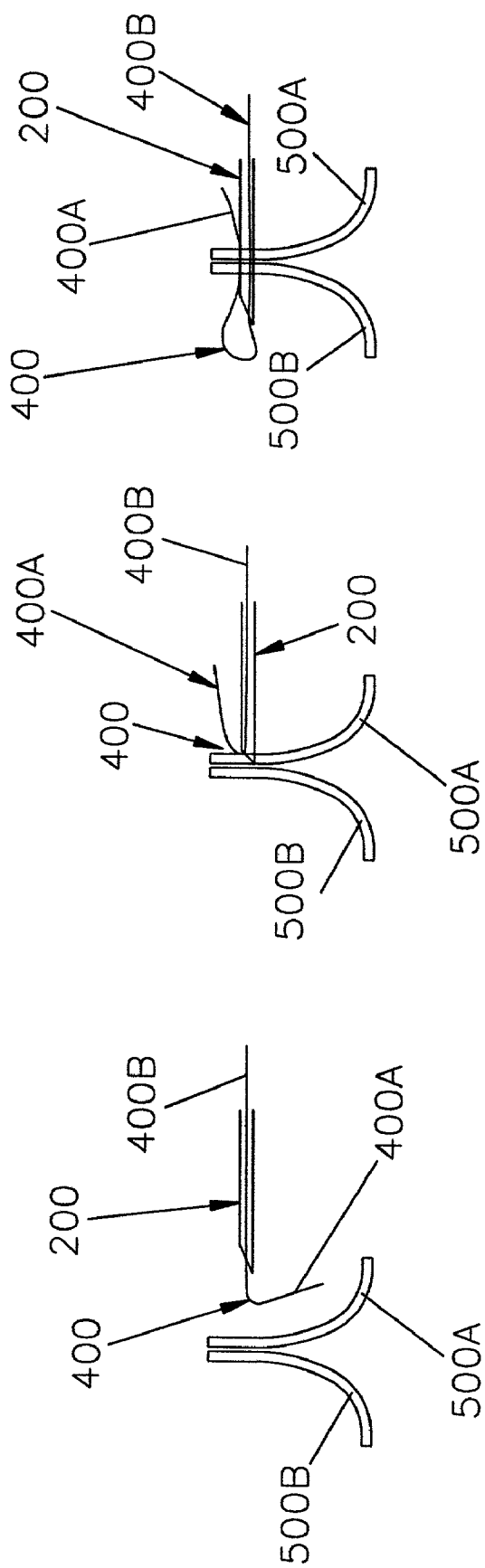
FIGS. 56–58 illustrate how a suture loop can be passed across two pieces of tissue using the present invention.

FIGS. 56–58 illustrate how a suture loop can be passed across two pieces of tissue using the present invention. More particularly, a length of suture 400 is first loaded onto suture passer 100 by feeding one end 400A of the suture into the suture passer's cannula 200. Suture end 400A extended all the way out the distal end of the cannula (see FIG. 56). Suture end 400A is then brought back to the suture passer's handle, so that the length of the suture will engage the blunted needle heel 274 as it exits from the cannula (see FIG. 57). Alternatively, suture end 400A could be left dangling until the force of tissue penetration brings suture end 400A back against the blunted needle heel 274. Suture length 400B is loaded onto the suture passer's proximal suture guide 304. The intermediate portion of suture 400 will extend along the handle's distal upper surface 310. Then the distal end of the suture passer's cannula 200 is forced through two pieces of tissue 500A and 500B until the distal end of the cannula exits the tissue. As this occurs, the suture will be carried through the tissue so that a loop of suture will reside on the far side of the tissue (see FIG. 58). Then the suture passer is withdrawn from tissue 500A and 500B, paying out the suture as it goes, so that both suture ends 400A and 400B will reside on the near side of the tissue, with a loop of suture remaining on the far side of the tissue.

Figures 59, 60, 61:
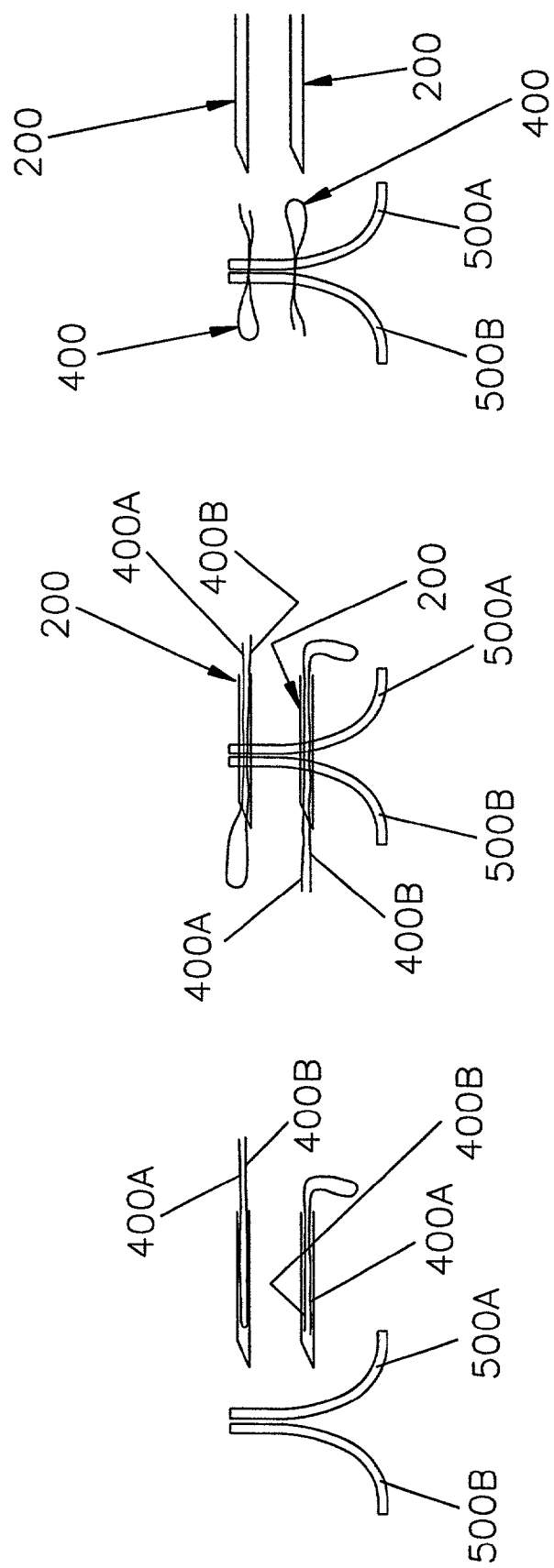
FIGS. 59–61 illustrate two different ways a folded suture loop can be passed across two pieces of tissue using the present invention.

FIGS. 59–61 illustrate two different ways a folded suture loop can be passed across two pieces of tissue using the present invention. More particularly, a portion of suture (i.e., either the two suture ends 400A and 400B, or the intermediate portion of suture extending between the two suture ends 400A and 400B) is placed inside the cannula 200 (see FIG. 59). Then the cannula is inserted through tissue 500A and 500B so that the distal end of the cannula emerges on the far side of the tissue. Next, the portion of suture previously held in the cannula (i.e., either the two suture ends 400A and 400B, or the intermediate portion of suture extending between the two suture ends 400A and 400B) is pushed outside the distal end of the cannula (see FIG. 60). Finally, the cannula is withdrawn from the tissue, leaving a loop of tissue residing on one side of the tissue and the two suture ends residing on the other side of the tissue (see FIG. 61).

FIGS. 62–64 illustrate how a simple stitch can be converted to a mattress stitch with a suture loop using the present invention. More particularly, a loop of suture 402 is first positioned on the far side of the tissue using the technique of FIGS. 56–58, and a single strand of suture 404 is passed through the tissue using the technique of FIGS. 53 and 54 (see FIG. 62). Then the end of suture 404 is drawn through the loop of suture 402 (see FIG. 63). Finally the loop of suture 402 is withdrawn back through tissue 500A, 500B, carrying the strand of suture 404 with it (see FIG. 64).

The foregoing description of the preferred embodiments of the invention has been presented for the purposes of illustration and description. It is not intended to be exhaustive or to limit the invention to the precise forms disclosed. Many modifications and variations are possible in light of the above teachings. It is intended that the scope of the invention not be limited by this detailed description.

What is claimed is:

1. A suture passer comprising:

a longitudinally extending hollow cannula having a central passage slidingly receivable of a surgical suture;

a manually graspable handle adapted to engage said hollow cannula for manipulation thereof, said handle having a distal end, a proximal end, and an intermediate portion;

first suture guide means formed by a first body portion of said handle proximate to the distal end of said handle and having a channel therethrough for guidingly holding the surgical suture;

second suture guide means formed by a second body portion of said handle proximal to said first suture guide means and having a channel therethrough for guidingly holding the surgical suture; and said intermediate portion having an exposed surface for supporting the surgical suture, the exposed surface being disposed between the first and second body portions and configured to expose the surgical suture.

2. A suture passer according to claim 1 further comprising means for disengaging said cannula from said handle.

3. A suture passer according to claim 1 wherein said hollow cannula includes a proximal portion, and further wherein said proximal portion of said cannula is receivable within a first bore formed in the first body portion of said handle, the bore terminating at a proximal opening adjacent to said exposed surface of said handle intermediate portion between said first and second body portions.

4. A suture passer according to claim 1 wherein said cannula is sharply pointed at a distal end thereof.

5. A suture passer according to claim 4 wherein said cannula is rounded off at a heel of the distal end so as to minimize the possibility of damaging suture during a tissue piercing operation.

* * * * *